United States Patent
Teuschl et al.

(10) Patent No.: US 10,214,571 B2
(45) Date of Patent: Feb. 26, 2019

(54) PRODUCT MADE OF SILK

(71) Applicant: Andreas Teuschl, Vienna (AT)

(72) Inventors: Andreas Teuschl, Vienna (AT); Martijn Van Griensven, Vienna (AT); Heinz Redl, Vienna (AT)

(73) Assignee: MorphoMed GmBH, Vienna (AT)

( * ) Notice: Subject to any disclaimer, the term of this patent is extended or adjusted under 35 U.S.C. 154(b) by 762 days.

(21) Appl. No.: 14/431,449

(22) PCT Filed: Sep. 27, 2013

(86) PCT No.: PCT/EP2013/070232
§ 371 (c)(1),
(2) Date: Mar. 26, 2015

(87) PCT Pub. No.: WO2014/049134
PCT Pub. Date: Apr. 3, 2014

(65) Prior Publication Data
US 2015/0239944 A1 Aug. 27, 2015

(30) Foreign Application Priority Data
Sep. 27, 2012 (EP) .................................. 12186272

(51) Int. Cl.
*C07K 14/435* (2006.01)
*D06M 11/05* (2006.01)
(Continued)

(52) U.S. Cl.
CPC ...... *C07K 14/43586* (2013.01); *A61L 27/227* (2013.01); *A61L 27/3604* (2013.01);
(Continued)

(58) Field of Classification Search
CPC ............ C07K 14/43586; A61L 27/227; A61L 31/047; A61L 31/005; A61L 27/3691; A61L 27/3687; A61L 27/3604; D06M 11/67; D06M 11/155; D06M 11/05; D06M 11/13; D06M 23/14; D06M 13/213;
(Continued)

(56) References Cited

U.S. PATENT DOCUMENTS 3,510,390 A 5/1970 Bjorksten et al.
8,202,379 B1 6/2012 Delong et al.

FOREIGN PATENT DOCUMENTS

| CN | 102430155 A | * | 5/2012 |
| CN | 101736430 B | | 7/2012 |
| GB | 12374 | | 7/1915 |

OTHER PUBLICATIONS

International Preliminary Report on Patentability [PCT/EP2013/070232] dated Aug. 25, 2015.
(Continued)

*Primary Examiner* — Elizabeth M Cole
(74) *Attorney, Agent, or Firm* — Edwin S. Flores; Daniel J. Chalker; Chalker Flores, LLP

(57) ABSTRACT

Disclosed is a method for the production of three-dimensional silk products, wherein a three-dimensional silk product is treated with a silk solvent for a limited period of time so that a partial disintegration of the silk product is obtained whereafter the partially disintegrated silk product is re-stabilized with physical β-sheet induction by a re-stabilizing solution.

24 Claims, 16 Drawing Sheets

Figure 3:
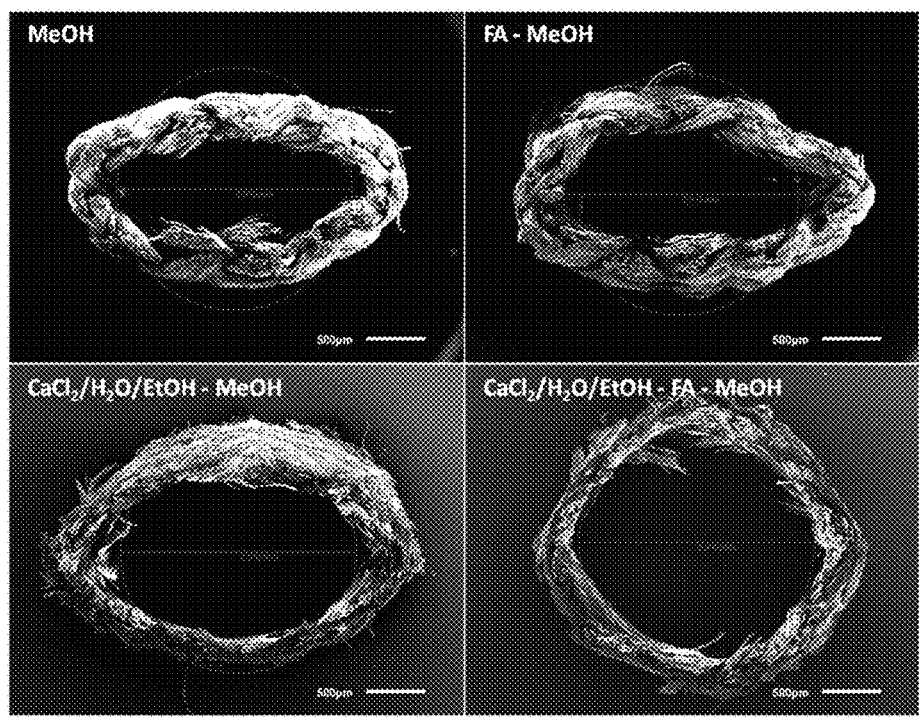

(51) Int. Cl.

| | | |
|---|---|---|
| D06M 11/13 | (2006.01) | |
| D06M 11/155 | (2006.01) | |
| D06M 11/65 | (2006.01) | |
| D06M 11/67 | (2006.01) | |
| D06M 13/144 | (2006.01) | |
| D06M 13/188 | (2006.01) | |
| D06M 13/21 | (2006.01) | |
| D06M 13/213 | (2006.01) | |
| D06M 23/14 | (2006.01) | |
| A61L 27/22 | (2006.01) | |
| A61L 27/36 | (2006.01) | |
| A61L 31/00 | (2006.01) | |
| A61L 31/04 | (2006.01) | |
| D06M 101/12 | (2006.01) | |

(52) U.S. Cl.
CPC ....... *A61L 27/3687* (2013.01); *A61L 27/3691* (2013.01); *A61L 31/005* (2013.01); *A61L 31/047* (2013.01); *D06M 11/05* (2013.01); *D06M 11/13* (2013.01); *D06M 11/155* (2013.01); *D06M 11/65* (2013.01); *D06M 11/67* (2013.01); *D06M 13/144* (2013.01); *D06M 13/188* (2013.01); *D06M 13/21* (2013.01); *D06M 13/213* (2013.01); *D06M 23/14* (2013.01); *D06M 2101/12* (2013.01); *Y10T 428/26* (2015.01); *Y10T 428/31728* (2015.04)

(58) Field of Classification Search
CPC .. D06M 13/21; D06M 13/188; D06M 13/144; D06M 11/65; D06M 2101/12; Y10T 428/31728; Y10T 428/26
See application file for complete search history.

(56) References Cited

OTHER PUBLICATIONS

Luke M Haverhals et al: "Natural Fiber Welding", Macromolecular Materials and Engineering, Wiley VCH Verlag, Weinheim, DE, vol. 295, Jan. 1, 2010 (Jan. 1, 2010), pp. 425-430.

Shahram Ghanaati et al: "Fine-tuning scaffolds for tissue regeneration: effects of formic acid processing on tissue reaction to silk fibroin", Journal of Tissue Engineering and Regenerative Medicine, vol. 4, No. 6, Jan. 28, 2010 (Jan. 28, 2010), pp. n/a-n/a.

Sung-Won Ha et al: "Dissolution of Bombyx m ori Silk Fibroin in the Calcium Nitrate Tetrahydrate-Methanol System and Aspects of Wet Spinning of Fibroin Solution", Biomacromolecules, vol. 4, No. 3, May 1, 2003 (May 1, 2003), pp. 488-496.

Extended European Search Report [EP] dated Mar. 13, 2015.

Written Opinion [PCT/EP2013/070232].

Ai, Hua et al., "Coating and Selective Deposition of Nanofilm on Silicone Rubber for Cell Adhesion and Growth" Cell Biochemistry and Biophysics 38 (2003) 103-114.

Bozkurt, A. et al. "CatWalk gait analysis in assessment of functional recovery after sciatic nerve injury" Journal of Neuroscience Methods 173 (2008) 91-98.

Deumens, Ronald et al. "The CatWalk gait analysis in assessment of both dynamic and static gait changes after adult rat sciatic nerve resection" Journal of Neuroscience Methods 164 (2007) 120-130.

Horan, Rebecca L. et al. "Yarn design for functional tissue engineering" Journal of Biomechanics 39 (2006) 2232-2240.

Hu, Xiao et al. "Regulation of Silk Material Structure by Temperature-Controlled Water Vapor Annealing" Biomacromolecules 2011, 12, 1686-1696.

Huang, W. L. et al. "Spinal cord compression and dorsal root injury cause up-regulation of activating transcription factor-3 in large-diameter dorsal root ganglion neurons" European Journal of Neuroscience, vol. 23, pp. 273-278, 2006.

Huang, W. et al. "Regenerative potential of silk conduits in repair of peripheral nerve injury in adult rats" Biomaterials 33 (2012) 59-71.

Karageorgiou, Vassilis et al. "Bone morphogenetic protein-2 decorated silk fibroin films induce osteogenic differentiation of human bone marrow stromal cells" J Biomed Mater Res 71A: 528-537,2004.

Kardestuncer, T. et al. "RGD-tethered Silk Substrate Stimulates the Differentiation of Human Tendon Cells" Clinical Orthopaedics and Related Research 2006 No. 448, pp. 234-239.

Kingham, Paul J. et al. "Adipose-derived stem cells differentiate into a Schwann cell phenotype and promote neurite outgrowth in vitro" Experimental Neurology 207 (2007) 267-274.

Lawrence, Brian D. et al. "Processing methods to control silk fibroin film biomaterial features" J Mater Sci (2008) 43:6967-6985.

Liu, Xiaohua et al. "Surface modification of interconnected porous scaffolds" J Biomed Mater Res 74A: 84-91, 2005.

Lovett, Michael L. "Gel spinning of silk tubes for tissue engineering" Biomaterials 29 (2008) 4650-4657.

Mondal, M. et al. "The silk proteins, sericin and fibroin in silkworm, *Bombyx mori* Linn.,—a review" Caspian J. Env. Sci. 2007, vol. 5 No. 2 pp. 63-76.

Murphy, Amanda R. et al. "Biomedical applications of chemically-modified silk fibroin" J. Mater. Chem., 2009, 19, 6443-6450.

Rowley, Jon A. et al. "Alginate hydrogels as synthetic extracellular matrix materials" Biomaterials 20 (1999) 45-53.

Schmidhammer, Robert et al. "Alleviated Tension at the Repair Site Enhances Functional Regeneration: The Effect of Full Range of Motion Mobilization on the Regeneration of Peripheral Nerves—Histologic, Electrophysiologic, and Functional Results in a Rat Model" J Trauma. 2004;56:571-584.

Schmidhammer, R. et al. "In peripheral nerve regeneration environment enriched with activity stimulation factors improves functional recovery" Acta Neurochir Suppl (2007) 100: 161-167.

* cited by examiner

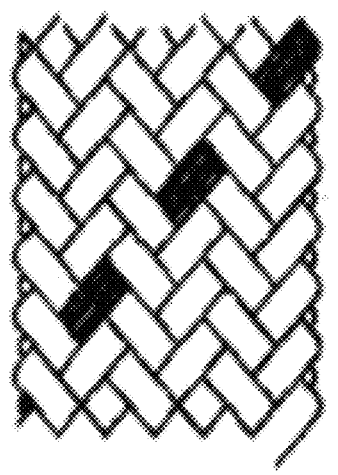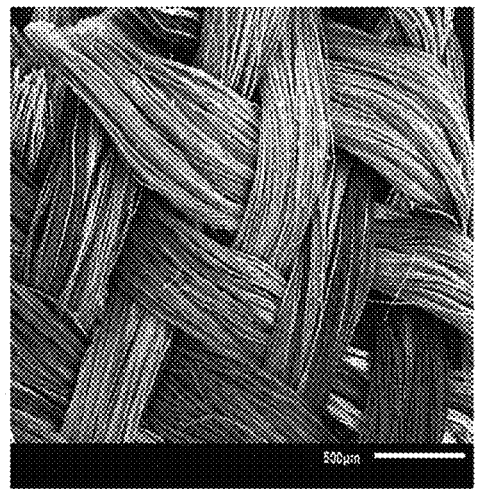
Fig.1
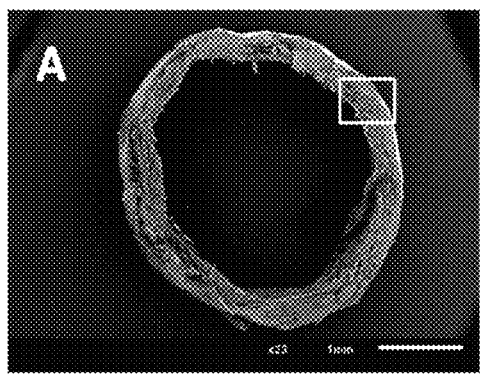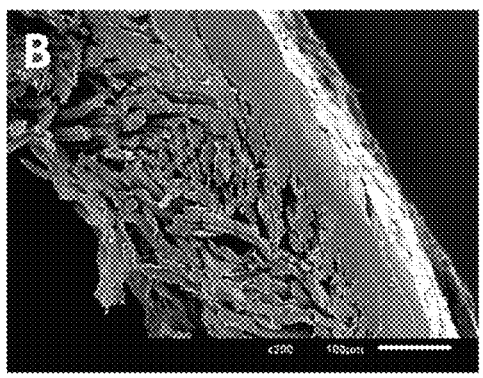
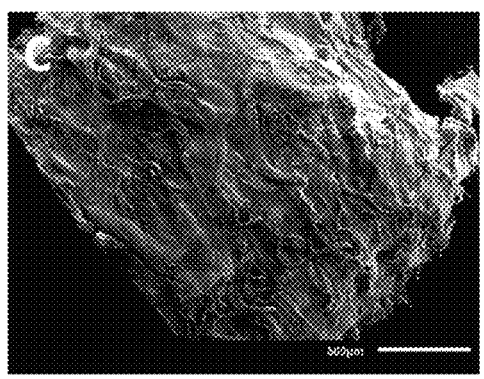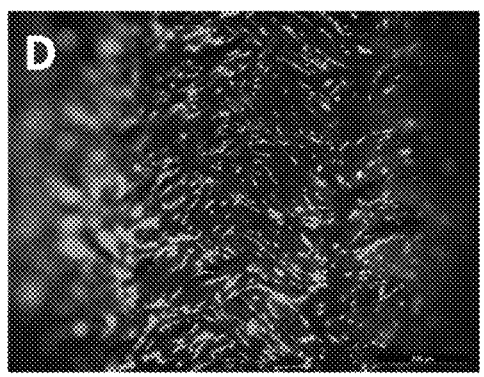
Fig.2

PRODUCT MADE OF SILK

The present invention relates to the field of processing silk material, specifically for providing silk material for medical use.

Historically, silk has been used in biomedical sutures for decades, where potential host immune responses have been observed. This may be the major concern with the use of silks that have led to its disregard for biomedical applications in the past. The main cause for eliciting immune response activation has been associated with sericin. Therefore, the adequate removal of sericin from raw silk is a critical step in the preparation of silk for tissue engineering and regenerative medicine applications to avoid biocompatibility problems.

The common silkworm silk, is obtained from the cocoons of the larvae of the mulberry silkworm *Bombyx mori*. The single silkworm cocoon fibre consists of two cores of fibroin surrounded by a glue-like protein called sericin, which fixes the fibroin fibres to each other. Fibroin and sericin account for about 75 and 25% wt., respectively.

Morphologically, silk fibroin is characterized by its highly oriented and crystalline fibrous structure. This structure is responsible for its insolubility in most solvents such as water, ethanol, dilute acids and bases. In contrast to fibroin the globular protein sericin is readily soluble in aqueous solvents. In textile industry the removal of sericin is also of great interest because the lustre of silk clothes is concealed by sericin. Therefore, research groups working on silk are not restricted to the biomaterial field but also the textile industry searches for optimal degumming methods. This fact leads to the existence of various degumming methods, including alkaline solutions w/o detergents, urea, tartaric acid, citric acid, or enzymes, such as papain or endopeptidase. The classical way of degumming is the boiling of the raw silk in alkaline solutions w/o detergents that assist in removing the sericin from the fibrous structure. It may be underlined that it is common to use 0.02 M sodium carbonate solution at 100° C. for 30-60 min to accomplish degumming, especially in the tissue engineering research field. Often, this alkaline degumming is carried out as batch treatment using soaps or detergents in addition to alkali.

Industrial silk production often involves solving the natural fibres into a fibroin solution and reprocessing the fibres from this solution by suitable processes, such as spinning.

The provision of silk material for medical uses almost exclusively employs dissolution of the silk fibres in aqueous systems such as LiBr or $CaCl_2$/EtOH/Water in a molar ratio of 1:2:8 (CN 101736430 B), followed by reprocessing the silk solution into desired material formats, e.g. by spinning, electrospinning, casting from aqueous or organic solvent systems, gelation, foaming, etc. (Vepari et al., 2007, U.S. Pat. No. 5,252,285 A; Sung-Won Ha et al., Biomacromolecules 4(3) 2003 p. 488-496).

However, these reprocessed silk materials from fibroin solutions differ from the natural (native) silk structures, often resulting in three-dimensional products with properties (specifically mechanical properties) which are not satisfactory for many possible uses, especially in the field of surgery.

To avoid these diminished properties of the resulting silk structures techniques are required that use degummed silk fibres as raw material. The high processability of silk fibres with textile engineering techniques such as braiding, knotting, weaving, etc., especially in the field of biomedical products, has been demonstrated by Horan et al. (J Biomech 39(12) 2006, p. 2232-2240). Despite the improvements one can get from using textile engineering techniques for scaffold production there are special cases where it can be beneficial to introduce bonding of fibres that are hardly or even not achievably with textile engineering techniques. Therefore different strategies have been developed that bond natural as well as synthetic fibers together using solvents, adhesives (embedding in resins) or applying heat (U.S. Pat. No. 3,510,390 A). One approach to reach such bonding of silk fibres to adjacent ones is to use ionic liquids. These ionic liquids serve as a solvent for many biopolymers including silk. For example Haverhals et al. (Macromolecular materials and engineering 295, 1 Jan. 2010, p. 425-430) could show that using 1-ethyl-3-methylimidazolium acetate it is possible to "weld" native and undegummed silk fibers together. This process is described and displayed to lead to surface bonds of the fibres with nondisrupted and non-disintegrated structures (U.S. Pat. No. 8,202,379 B1).

Another chemical reagent that has been used to stick silk fibres to each other is formic acid. Already in 1915 it was described in a process to produce uniform fibre pulp from short silk fibres (GB 12374 A). In the biomedical field Ghanaati et al. (JTERM, 2010 (4) p. 464-472) used formic acid to bond degummed and non-woven silk fibres together to get implantable stable scaffolds but without creating a continuous phase of fused silk fibres.

It is clear that biomaterials, specifically those which are implanted must have significant mechanical stability, especially for resisting pressure forces and any unintended collapsing of such material must be prevented or excluded. Accordingly, improved methods are needed to provide robust biomaterials based on silk with improved mechanical and morphological properties. These methods should enable a robust, reproducible and reliable production method; on the other hand, the products must allow the biomaterials produced to be applicable especially in medicine and in cell culture methods.

It is therefore an object of the present invention to provide such a method; such method should also be specifically suitable for medical purposes, especially for therapy and surgery.

Therefore, the present invention provides a method for the production of three-dimensional silk products, wherein a three-dimensional silk product is treated with a silk solvent for a limited period of time so that a partial disintegration of the silk product is obtained whereafter the partially disintegrated silk product is re-stabilised with physical β-sheet induction.

Within the present invention, "three-dimensional silk products" shall not only be understood as products having none of the three dimensions being irrelevant compared to the other two but as products that are defined as at least a stack of two layers of fibroin, a homogeneous fibroin layer (region, area, phase, etc.) and a fibrous fibroin layer sterically allowing the generation of anisotropic material properties.

The method according to the present invention provides silk constructs, especially fibroin constructs, with improved mechanical properties. This allows implanting the products obtainable by the present process in vivo into regions where they are exposed to specific mechanical influences. For example in the case of a nerve conduit, in vivo implants may be exposed to pressure forces which may cause collapse of such implants. In such a case, a (woven) tube of untreated fibroin would collapse and hinder a growing nerve covered by such tube. The method according to the present invention allows provision of transplants resisting such forces causing crush or contusion. Whereas the disintegration step as well as the restabilising step has been carried out before on fibroin constructs without obtaining products with the advantageous properties according to the present invention, it is the combination of these two steps that results in the improved properties of the products according to the present invention.

The partial disintegration step according to the present invention can be seen as a partial melting of the silk product in the area exposed to the disintegration solution, the silk solvent. This involves a partial disorganisation of the beta-sheet structure of fibroin which makes fibroin shapeable. The disintegration can be performed to the extent which is desired for the final product, e.g. only close to the surface or through the whole silk product, of course without transforming the product into a solution. The general shape of the starting material (i.e. the silk product) is essentially retained throughout the partial disintegration step. Therefore, the silk solvent is only applied for a limited period of time and not until the solvation is completed (and equilibrium is achieved). A complete liquefaction of the silk (fibroin) material (again) into a solution or suspension does not take place according to the present invention, only a partial de-solidification process in a limited area of the product. This (partial) "melting" step enables a denser packaging of the fibroin molecules in the disintegrated area of the product characterized by the formation of a continuous phase. The extent to which the disintegration step is allowed to be performed on the silk product is then responsible for the different product characteristics of the final product according to the present invention.

It is therefore clear that "disintegration" according to the present invention is clearly distinct from other silk processing steps, such as degumming ("degumming" would refer to the separation of two protein classes from each other (i.e. sericin is separated from fibroin fibrils) which is similar to removal an outer sheet from a core).

In the re-stabilising step, the disintegrated portion of the silk product is solidified again, however, resulting in an area with different morphological and mechanical properties as the non-disintegrated part of the silk product. With the re-stabilising step, the silk product completely solidifies again, however, usually resulting in an anisotropic final product wherein the surface that has been most prominently exposed to the silk solubilising solution has undergone the most extensive structural change whereas the inner portions of the silk product (or a surface which has not been exposed to the silk solubilising solution ("silk solvent")) could remain almost unchanged or at least not changed to the extent of the area which was more exposed to the silk solvent. The re-stabilising step according to the present invention is therefore the induction of a morphological crystalline-like state. The re-stabilising step is performed by a physical β-sheet induction. The disintegration has caused a "random" structure of the silk. Thereafter, the disintegrated silk is physically treated to achieve a β-sheet refolding. The typical way for performing this step is to remove water molecules from the disintegrated areas within the random silk form until such re-folding occurs.

Silk fibroin is a polymorphous material existing in three different phases, commonly identified as silk I, II and III. Silk I represents a state of helical and random coil structures that is water-soluble and can be found in the glands of the silkworm prior to the spinning process or as (aqueous) silk solution (also known as regenerated silk). Silk II is characterized by its asymmetrical β-sheet structures in which hydrogen side chains from glycine are mainly exposed on one side of the β-sheet and hydrophobic methyl side chain from alanines on the other. As a consequence, β-sheets self-assemble by aligning side-by-side, stabilized by strong hydrogen bonds and van der Waals forces.

By exposure to heat or shearing forces, a structural change from silk I to silk II is induced. This phase transition can also be obtained by the treatment of silk structures with methanol or other reagents that promote water loss from the silk molecules. As a consequence the transition from random coil (silk I) to β-sheet formation (silk II) is induced by enhanced chain-chain interactions. Beside the phase transition, this process also guarantees water-stable silk structures. Further processes to induce and control beta-sheet formation are steam-autoclaving (Park et al., J. Mat. Sci 43 (2008), 6967-6985) and water annealing methods (Hu et al., Biomacromol. 12 (2011), 1686-1696).

The re-stabilising step is preferably performed according to the present invention by treatment with a re-stabilising solution. Also combinations of different re-stabilising solutions can be applied.

Re-stabilising by treatment with a re-stabilising solution can be performed with any solution which achieves β-sheet formation of silk. Such crystallinity (re-stabilisation by treatment with a re-stabilising solution) is usually induced via two methods in current industrial methods, either by immersion in an alcohol such as methanol or ethanol. Alcohol immersion is simple and quick but if the use of an alcohol should be avoided, alcohol-free re-stabilising solutions such as formic acid can be used.

As a test system for the present invention, silk fibroin control structures for nerve repair were investigated. More specifically, bridging of a defect of N. ischiadicus was observed in rats in vivo and showed surprising results (see example section).

It was surprisingly found in the course of the present invention that silk products, especially three-dimensional fibroin products, can be efficiently improved with respect to their mechanical properties, especially their resistance towards collapsing after in vivo implantation, with the application of the two processing steps according to the present invention. This allows the production of a three-dimensional silk product with significant advantages and possibilities compared to silk fibres which have been reprocessed from fibroin solutions (not having this reinforcement step according to the present invention).

The provision of more robust complex silk structures according to the present invention provides a significant advantage in modern surgery. Also the production process as a whole is reliable and suitable for industrial mass production.

Preferably, the silk solvent according to the present method comprises LiBr, LiSCN, hexafluoro-2-propanol (HFIP), a mixture comprising ethanol and $CaCl_2$ or a mixture comprising methanol and calcium nitrate; or mixtures thereof. According to a preferred embodiment, LiBr is used in the silk solvent in a concentration of 1 to 10 M, preferably 3 to 10 M, especially 5 to 7 M. According to a preferred embodiment, LiSCN is used in a concentration of 1 to 17.5 M, preferably 5 to 15 M, especially 8 to 12 M. According to a preferred embodiment, HFIP is used in an solution containing 1 to 100% (v/v), preferably 50 to 100% (v/v) HFIP, especially 90 to 100% (v/v) HFIP. Ethanol may e.g. be used in the silk solvent in an aqueous solution containing 1 to 50% (v/v) ethanol, preferably 5 to 40% (v/v) ethanol, especially 10 to 30% (v/v) ethanol. $CaCl_2$ may e.g. be used in the silk solvent in a molar ratio of 1:0.3 to 1:3 with respect to ethanol (i.e. 1 mol $CaCl_2$:0.3 mol EtOH to 1 mol $CaCl_2$:3 mol EtOH), preferably 1:1 to 1:2.5, especially 1:1.5 to 1:2.2.

The present method is applicable to a vast variety of different silk products, especially fibroin products. Preferably, the three-dimensional silk product is a woven fabric, a non-woven fabric, a tube, a knitted product or a pressed product. Although the method according to the present invention can be conducted with any silk scaffold, the method is specifically suitable for the treatment of scaffolds made up of silk fibres. Those products can be transformed into silk scaffolds with a region wherein disintegration has taken place and regions wherein the original silk fibre structure is still present, preferably providing an anisotropic product, i.e. a product with a surface which has been disintegrated and an inner portion which still contains the silk fibres. It is specifically preferred to use a silk fibroin product or a woven product of natural silk fibres. Preferred starting materials for the method according to the present invention are e.g. silk tubes (e.g. as produced by Lovett et al., Biomaterials 29 (2008), 4650-4657; US 2008/249639 A1; Ghaznavi et al., Ann. Pl. Surg. 66 (2011), 273-279), silk fabrics (e.g. as produced by WO 02/29141 A1), or silk membranes (e.g. US 2010/286774 A1).

The silk material may be taken from all natural and synthetic sources; however, it is preferred to use silk products which are made of or derived of natural silk fibres from silkworm (*Bombyx mori*) cocoon. These fibres (in their natural form or already degummed (i.e. after removal of sericin from the fibres)) can either be used as natural fibres to produce the silk product used as starting material for the present method or transformed into a fibroin solution first and then re-processed (e.g. by spinning) again to a (fibroin) fibre and a fibroin product. The major industrial source for silk fibres is, of course, the mulberry silkworm *Bombyx mori*, however, silk fibres from other silkworms (Lepidopteron) can also be used in the process according to the present invention. Silkworms can generally be distinguished in mulberry (*Bombyx mori, Bombyx mandarina*) and non-mulberry (*Antheraea* (A.) *mylitta, A. proylei, A. pernyi, A. yamamai, A. frithi, A. assamensis, Samia ricini, A. atlas, Gonometa postica, Cricula trifenestrata*) silkworms. Pattern-similarity of amino acid composition of extracted sericin between wild silkworms and domesticated silkworms are at least 97%, which demonstrates the high number of conserved amino acid sequences among different species of silkworms (Mondal et al., Caspian J. Env. Sci. 5 (2007), 63-76) and serves as a hint that the described method is also applicable to other silk sources.

On the other hand, it may also be preferred to apply the method according to the present invention on a silk product that is made of reconstituted fibres made of fibroin solutions, especially recombinant fibroin solutions.

The method according to the present invention has been specifically optimised for products being made up of silk fibers from the *Bombyx mori* silkworm. This is also the main industrial source of native silk fibres for textile industry. However, as already stated above, also other silk fibres, such as from other moth caterpillars or orb-spinning spiders (such as Nephila clavipes), can be used for the production of the silk products according to the present invention. It is also possible to apply the present method to a three-dimensional silk product which contains—besides silk material (fibres)—also other substances which are used for providing biocompatible materials, such as PEG, gelatin, collagen, hyaluronic acid, chitosan, etc., provided that the procedural steps are applied to these individual combinations without substantial destruction of the three-dimensional shape of the product.

Most preferred native silk fibres are those from *Bombyx mori* silkworm cocoon. Silk fibers from the *Bombyx mori* silkworm have a triangular cross section with rounded corners, 5-10 µm wide. The fibroin-heavy chain is composed mostly of beta-sheets, due to a 59-mer amino acid repeat sequence with some variations. The flat surfaces of the fibrils reflect light at many angles, giving silk a natural shine. The cross-section from other silkworms can vary in shape and diameter: crescent-like for Anaphe and elongated wedge for tussah. Silkworm fibers are naturally extruded from two silkworm glands as a pair of primary filaments (brin), which are stuck together, with sericin proteins that act like glue, to form a bave. Bave diameters for tussah silk can reach 65 µm.

Preferred silk products to be made with the method according to the present invention are medical implants, preferably a stent, a nerve conduit, a (tissue) scaffold (e.g. tendon, bronchi, trachea, etc.), a hernia meshwork, a ligature, especially an anterior cruciate ligament (ACL), or a cartilage and bone graft.

Figure 13A:
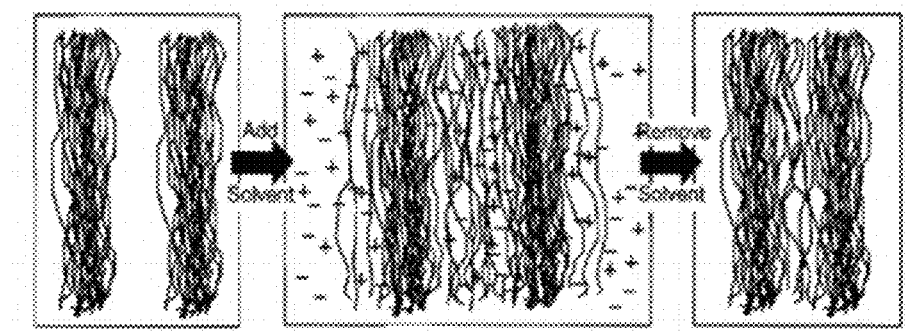
Figure 13B:
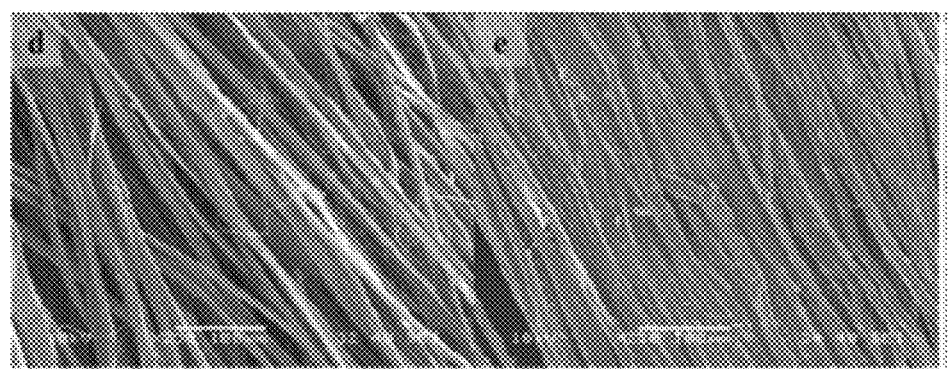
Figure 13C:
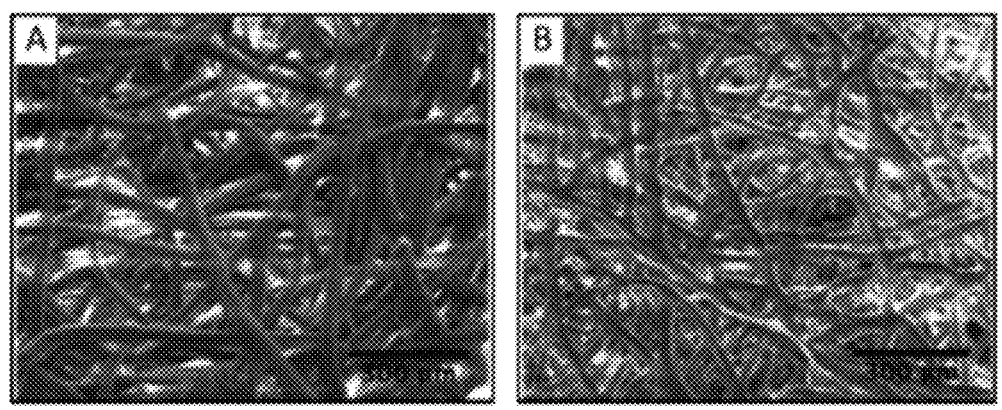

With the method according to the present invention it is possible to provide anisotropic silk products, i.e. products which have changing silk material properties on different sides or in different areas of or within a given product. The anisotropic three-dimensional silk product according to the present invention is characterised by at least a stack of two layers ("phases", "regions", "areas") of fibroin filaments sterically allowing the generation of anisotropic material properties. The three-dimensional material according to the present invention is also characterised by a homogeneous (continuous) fibroin phase (the region in the product that has been solved and was re-stabilised thereafter), which does not contain cavities ("entrapped cavities") or at least less than 5% v/v of entrapped cavities, and a fibrous fibroin phase (the region where the silk fibers have not been dissolved), which is not continuous but is characterised by the fibrous nature of the silk fibers (see FIGS. 11E-11I in contrast to FIG. 13 showing prior art products with no homogeneous fibroin phase (but structures of filamentous nature ("stacked fibers", "continuous filaments", etc.)); the red bar in FIGS. 11E-11I showing the thickness of the homogeneous phase in the products according to the present invention).

The products according to the present invention can be anisotropic by having an outer layer being continuous and an inner layer being filamentous. It is also possible that only the inner core of a product is present in filamentous form whereas the surface of the whole product is homogeneous, or even the whole product is non-filamentous and in a homogeneous and continuous form. The area on the surface of the product that should not be made homogeneous can be protected from the silk solvent and the re-stabilising solution during the process, e.g. by physical covering or chemical protection.

This can be achieved e.g. by directing the solubilising solution only on one side of the silk product so that only one side is processed according to the present invention whereas the opposite side is not or not significantly subjected to this treatment. This then results in a product with two different surfaces having different properties (e.g. one side still having the untreated properties and the other side having the properties of the silk products according to the present invention. It is also possible to provide anisotropic properties of a product by allowing the partial disintegration to take place until a certain "depth" of the silk product so that the interior part of the silk products retains its untreated nature and only the surface (down to the desired "depth") exhibits the improved changed properties according to the present invention (see e.g. FIG. 2). Since the method according to the present invention allows conducting the treatment with the silk solvent for partial disintegration e.g. for shorter or longer times (or by changing other process parameters, such as temperature, concentration or process chemicals, etc.), the "depth" up to which the disintegration takes place may be directed. For example, each silk product may either be treated only shortly (with only the immediate surface disintegrated and immediately reinforced by the re-stabilising step) or for extended durations (allowing most of the silk product being disintegrated in the first step (and reinforced by the re-stabilising step according to the present invention which is always conducted after disintegration has been performed, preferably immediately thereafter)).

In general, the three-dimensional products according to the present invention are complex three-dimensional structures having a diameter in the smallest dimension ("thickness") of at least 0.1 mm, preferably 0.5 mm. Theoretically, also thicknesses of 10-15 μm are possible, however, such embodiments are usually of low practicability. They can also be made by folding, welding or tubing of simpler three dimensional products. In fact, preferred three-dimensional products according to the present invention have a diameter in the smallest dimension of at least 1.0 mm, preferably of at least 2.0 mm, especially of at least 5.0 mm.

The process parameters for the solubilising step and the re-stabilising steps may easily be optimised for the specific product to be obtained in a reproducible manner. Temperatures, type and concentrations of the disintegration and re-stabilising chemicals, durations of treatment may be adapted for each product depending on the amount of disintegration and reinforcement degree the final product should have. For example, the treatment with a silk solvent may be carried out at a temperature of 20 to 100° C., preferably 50 to 78° C., especially 70 to 77° C. Preferred embodiments apply a duration of the treatment with a silk solvent e.g. for 1 s to 2 h, preferably 1 s to 0.5 h, especially 10 s to 30 min. The treatment with a re-stabilising solution may e.g. be carried out for 1 s to 1 h, preferably 5 min to 1 h, especially 20 min to 30 min. It is, of course, clear that temperature applied and time duration are dependent on each other and have to be adjusted to each other individually for a given production set-up (higher temperature usually allows shorter reaction times).

A preferred re-stabilising agent is formic acid. Formic acid is known to be a silk solvent as well as a silk cristallising agent (Um et al. Int. J. Biol. Macromol 33 (2003) 203-213). In the re-stabilising agent according to the present invention, formic acid acts as a weak solvent which causes random-coil structure of formic acid which itself leads to a hydrodynamic radius of the silk fibroin molecules. This leads to a preordered/denser package before cristallisation. The final cristallisation may then be achieved by the methods known in the art, e.g. (and most preferred) by treatment with methanol. Other re-stabilising solvents may be acetic acid, ethanol, propanoic acid, halogenated organic acids with 1 to 4 carbon atoms, e.g. FCOOH, ClCOOH, $CF_3COOH$, $CF_2HCOOH$, $CFH_2COOH$, $CCl_3COOH$, $CCl_2HCOOH$, $CClH_2COOH$, etc., especially acetic acid. The preferred re-stabilising agent is, as stated above, formic acid, preferably 90 to 100% formic acid, especially 97 to 99% formic acid. A specifically preferred embodiment of the present invention applies % formic acid which is a well-defined basic chemical compound.

In the method according to the present invention, the silk fibers are dissolved by the silk solvent to obtain a three-dimensional product with a region wherein the silk fibers have been dissolved and wherein the fibroin is therefore present as random coils. The re-stabilising solution, especially formic acid, then induces formation of β-sheets (continuous phase); fibroin is stabilised by this β-sheet formation. Preferred further treatment with cristallising agents, especially methanol, leads to the stabilization of the continuous fibroin phase that is water-insoluble.

A specifically preferred embodiment of the present invention is a method wherein the silk solvent is a combination of $CaCl_2$, ethanol and water and wherein partially disintegrated silk product is re-stabilised with formic acid and wherein the product so obtained is further treated with methanol as a final re-stabilising step. This combination of steps enables a product with significantly improved mechanical properties (see e.g. FIG. 3).

According to a preferred embodiment, the three-dimensional silk product is provided with resolvable non-silk material which can be removed from the re-stabilised product, preferably wherein the resolvable non-silk material are polymers (e.g. polyethylene glycol), polysaccharides/sugars, salts, or in general any substance used as soluble porogen. This material can—after the product according to the present application has been disintegrated—be resolved to leave spaces in the product which can be useable as containments for cells or pharmaceutically active substances or provide space for growth of tissue, e.g. blood vessels, especially capillaries.

According to a preferred embodiment of the present invention, the silk product is equipped with further active molecules. With such active molecules, valuable and important features can be added to the silk product according to the present invention. For example, molecules with cell adhesion promoting properties (or cell adhesion preventing properties) can be added to the silk product. A preferred three-dimensional silk product further comprises substances which promote cell adhesion, preferably cell-binding peptides, especially Arg-Gly-Asp ("RGD") peptides; cell adhesion promoting proteins, especially SF protein, gelatin, fibronectin or lectin. Preferably, the three-dimensional silk product further comprises modified polypeptides which promote cell adhesion, especially modified RGD peptides, SF protein, gelatin, fibronectin or lectin. In general, the promotion of cell adhesion onto surfaces of biomaterials is of great interest for tissue engineering applications. Many attempts have been made to tailor material surfaces with bioactive molecules such as cell-binding peptide sequences including arginine-glycine-aspartic acid or biomolecule-derived substances such as gelatin or fibronectin to improve cell adhesion (Rowley et al., Biomat. 20 (1999), 45-53; Liu et al., J. Biomed. Mat. Res. A 74 (2005), 84-91). SF is a protein of more than 5000 amino acids (accession number P05790) mainly composed of repetitive motifs of glycine and alanine. Nevertheless, SF does contain a sufficient fraction of reactive amino acids such as aspartic and glutamic acid, tyrosine, serine and threonine, all accessible for chemical modifications (Murphy et al., J. Mat. Chem. 19 (2009), 6443-6450). For example, carbodiimide binding chemistry has been used to couple silk fibroin with bone morphogenetic protein 2 (BMP-2) to induce bone formation (Karageorgiou et al., J. Biomed. Mat. Res. A 71 (2004), 528-537), and to RGD peptide to promote cell attachment (Kardestuncer et al., Clin. Orthop. Rel. Res. 448 (2006), 234-239). Additional molecules that can be used to decorate silk fibroin and improve cell adhesion are lectins, various forms of RGD-sequences, binding motifs similar to collagen, fibronectin or other natural proteins.

According to another aspect, the present invention also refers to the three-dimensional silk products which are obtainable by a method according to the present invention.

As already stated, these products have improved mechanical properties, especially an improved resistance against pressure or collapsing forces. This makes the products according to the present invention specifically suitable for providing medical devices in tubular form, especially in vivo implantation tubes, such as vascular grafts or nerve conduits, or other scaffolds. Accordingly, preferred products according to the present invention are stents, vascular grafts, nerve conduits, hernia meshworks, or any other scaffold for tissue engineering or regenerative medicine applications.

The extent of the partial disintegration carried out on the silk product according to the present invention (and, of course, the subsequent re-stabilising of this disintegrated regions in the product) may be exactly directed by the method according to the present invention, preferably by the time duration for the treatment with the silk solvent. For example, a treatment for about 20 s leads to a disintegration depth of about 50 μm; a 40 s treatment leads to a disintegration of about 100 μm from the surface of the silk product which is exposed to the silk solvent. The surface of the silk product which is exposed to the silk solvent is, of course, completely disintegrated. The depth of the disintegrated regions of the silk product is then adjustable, e.g. by the duration of exposure of this surface to the silk solvent. The silk products according to the present invention therefore have regions wherein this disintegration was performed and regions wherein the disintegration has not been taken place. These regions are usually clearly separated in the final product (i.e. after re-stabilising) by a small boundary region (see also examples wherein these boundary regions are visible). Whereas the products according to the present invention usually exhibit at least one surface with complete disintegration (with a certain depth of disintegrated regions), also non-disintegrated regions are present (usually on the opposite side of the surface which was exposed to the disintegration solution (i.e. the silk solvent)).

Preferably, the depth of disintegration (in the final product visible as the depth to which the fibroin has been re-stabilised (and crystallised) and appears as dense mass (in contrast to the fibroin fibres still visible in the portion of the silk product which has not been disintegrated; i.e. the homogeneous or continuous fibroin phase)) is 5 μm or more in order to provide a silk product which shows the improved mechanical and morphological characteristics of the present invention, e.g. a flexible stability and/or a closed surface. Product with a depth of disintegration of e.g. about 1 μm or less could show cracks or less robust mechanical properties. Depending on the planned use of the silk products according to the present invention, the depth of disintegration is preferably 20 μm or more, more preferred 50 μm or more, especially 100 μm or more. In specifically preferred embodiments of the present invention, the silk product has a depth of disintegration of at least 10% of the total thickness of the silk product, meaning that at least 10% of the total thickness of the silk product is disintegrated (from the exposed surface inwards to the silk product). Even more preferred products exhibit a depth of disintegration of at least 20%, especially at least 30%. The "depth of disintegration" is visible in the final product in cross section as the distance from the surface to the end of the re-stabilized (and crystallised) regions in the product. The "end of the re-stabilised regions" is also the beginning of the region wherein no disintegration took place and wherein the silk fibres are present in their original shape and can be clearly distinguished from each other. The "depth of disintegration" is practically the diameter of the homogeneous fibroin phase (with no or less than 5% v/v entrapped cavities) in the final product; the rest is practically the filamentous fibroin phase in the final product. At the border between the continuous and the filamentous phase, mixed phases or regions are present, depending on the reaction conditions applied and on the thickness and nature of the starting material. Such mixed regions have usually more than 5% v/v cavities and have silk fibers at least partially stacked together, however, usually with non-disintegrated structures.

Also the two-dimensional silk products which are obtainable by the method according to the present invention have new and advantageous properties, especially mechanical and morphological properties. Specifically preferred is a two-dimensional product in sheet form, preferably for medical use, especially a film, a membrane, a woven sheet or a mesh for cell attachment, spreading, growth and differentiation.

On the other hand, the method according to the present invention can be used to produce cell culturing material, e.g. a cell substratum (for culturing cells) upon which cells can be seeded for further growth or production of cellular components (e.g. recombinant proteins or other substances which are secreted out of the cells).

Preferred embodiments of the present invention can therefore be defined as follows:

1. Method for the production of three-dimensional silk products, wherein a three-dimensional silk product is treated with a silk solvent for a limited period of time so that a partial disintegration of the silk product is obtained whereafter the partially disintegrated silk product is re-stabilised with physical β-sheet induction.

2. Method according to embodiment 1, wherein the silk solvent comprises LiBr, LiSCN, 1-ethyl-3-methylimidazoliumacetate, hexafluoro-2-propanol (HFIP), a mixture comprising ethanol and $CaCl_2$ or a mixture comprising methanol and calcium nitrate; or mixtures thereof.

3. Method according to embodiment 1 or 2, wherein LiBr is used in a concentration of 1 to 10 M, preferably 3 to 10 M, especially 5 to 7 M.

4. Method according to any one of embodiments 1 to 3, wherein LiSCN is used in a concentration of 1 to 17.5 M, preferably 5 to 15 M, especially 8 to 12 M.

5. Method according to any one of embodiment 1 to 4, wherein HFIP is used in an solution containing 1 to 100% (v/v), preferably 50 to 100% (v/v) HFIP, especially 90 to 100% (v/v) HFIP 6. Method according to any one of embodiments 1 to 5, wherein ethanol is used in an aqueous solution containing 1 to 50% (v/v) ethanol, preferably 5 to 40% (v/v) ethanol, especially 10 to 30% (v/v) ethanol.

7. Method according to any one of embodiments 1 to 6, wherein $CaCl_2$ is used in the silk solvent in a molar ratio of 1:0.3 to 1:3 with respect to ethanol, preferably 1:1 to 1:2.5, especially 1:1.5 to 1:2.2.

8. Method according to any one of embodiments 1 to 7, wherein calcium nitrate is used in the silk solvent in a molar ratio of 1:0.3 to 1:6 with respect to methanol, preferably 1:3 to 1:4.5, especially 1:3.5 to 1:4.2.

9. Method according to any one of embodiments 1 to 8, wherein the three-dimensional silk product is a woven fabric, a non-woven fabric, a tube, a knitted product or a pressed product.

10. Method according to any one of embodiments 1 to 9, wherein the silk product is a silk fibroin product or a woven product of natural silk fibres, especially wherein the silk product is made of fibres from silkworm (*Bombyx mori*) cocoon.

11. Method according to any one of embodiments 1 to 10, wherein the silk solvent is a combination of $CaCl_2$, ethanol and water and wherein partially disintegrated silk product is re-stabilised with formic acid and wherein the product so obtained is further treated with methanol as a final re-stabilising step.

12. Method according to any one of claims 1 to 11, wherein the silk product is made of reconstituted fibres made of fibroin solutions, especially recombinant fibroin solutions.

13. Method according to any one of embodiments 1 to 12, wherein the silk product is a medical implant, preferably a stent, a vascular graft, a nerve conduit, a (tissue) scaffold (e.g. tendon, bronchi, trachea, etc.), or a hernia meshwork.

14. Method according to any one of embodiments 1 to 13, wherein the partial disintegration is used to provide an anisotropic silk product or/and generate increased mechanical properties (e.g. elastic properties).

15. Method according to any one of embodiments 1 to 14, wherein the treatment with a silk solvent is carried out at a temperature of 20 to 100° C., preferably 50 to 78° C., especially 70 to 77° C.

16. Method according to any one of embodiments 1 to 15, wherein the treatment with a silk solvent is carried out for 1 s to 2 h, preferably 1 s to 0.5 h, especially 10 s to 30 min.

17. Method according to any one of embodiments 1 to 16, wherein the partially disintegrated silk product is re-stabilised with a re-stabilising solution.

18. Method according to embodiment 17 wherein the treatment with the re-stabilising solution is carried out for 1 s to 1 h, preferably 5 min to 1 h, especially 20 min to 30 min.

19. Method according to embodiment 17 or 18, wherein the re-stabilising solution is formic acid, preferably 90 to 100% formic acid, especially 97 to 99% formic acid.

20. Method according to any one of embodiments 17 to 19, wherein the re-stabilising solution is acetic acid, propanoic acid, halogenated organic acids with 1 to 4 carbon atoms, preferably FCOOH, ClCOOH, $CF_3COOH$, $CF_2HCOOH$, $CFH_2COOH$, $CCl_3COOH$, $CCl_2HCOOH$ or $CClH_2COOH$, especially acetic acid, or mixtures thereof.

21. Method according to any one of embodiments 1 to 20, wherein the partially disintegrated silk product is re-stabilised by steam autoclaving.

22. Method according to any one of embodiments 1 to 21, wherein the partially disintegrated silk product is re-stabilised or by water annealing.

23. Method according to any one of embodiments 1 to 22, wherein the three-dimensional silk product further comprises substances which promote peptide (e.g. modification with transglutaminase substrate sequences) or cell adhesion, preferably cell-binding peptides, especially Arg-Gly-Asp ("RGD") peptides; cell adhesion promoting proteins, especially SF protein, gelatin, fibronectin or lectin.

24. Method according to any one of embodiments 1 to 23, wherein the three-dimensional silk product further comprises modified polypeptides which promote cell adhesion, especially modified RGD peptides, SF protein, gelatin, fibronectin or lectin.

25. Three-dimensional silk product, obtainable by a method according to any one of embodiments 1 to 24.

26. Three-dimensional silk product according to embodiment 25, wherein the product is a stent, a vascular graft, a nerve conduit, a (tissue) scaffold (e.g. tendon, bronchi, trachea, etc.), or a hernia meshwork.

27. Three-dimensional silk product comprising a continuous (homogeneous, crystalline) silk region and a silk region with silk fibres.

28. Three-dimensional silk product according to embodiment 27, obtainable by a method according to any one of embodiments 1 to 24.

29. Three-dimensional silk product according to any one of embodiments 25 to 28 comprising a crystalline silk region and a silk region with silk fibres, wherein the crystalline silk region extends to at least 5 µm, preferably at least 20 µm, more preferred at least 50 µm, especially at least 100 µm, from the surface of the silk product.

30. Three-dimensional silk product according to any one of embodiments 25 to 29, wherein the silk product has additionally been treated mechanically.

31. Three-dimensional silk product according to embodiment 30, wherein the mechanical treatment is an embossing step.

32. Three-dimensional silk product according to any one of embodiments 25 to 31 comprising a crystalline silk region and a silk region with silk fibres, wherein the crystalline silk region extends from the surface of the silk product to at least 10%, preferably at least 20%, especially at least 30%, of the total thickness of the silk product.

33. Three-dimensional silk product according to any one of embodiments 25 to 32 wherein the three-dimensional silk product is provided with resolvable non-silk material which can be removed from the re-stabilised product, preferably wherein the resolvable non-silk material is are polymers (e.g. polyethylene glycol), polysaccharides/sugars, salts, or in general any substance used as soluble porogen.

The present invention is further illustrated by way of the following examples and the drawings, yet without to be limited thereto.

FIG. 1 shows braiding design (left image) and scanning electron micrograph (right image) of the braided tubular structure.

FIG. 2 shows micrographs of silk fibroin nerve guidance conduits (SF-NGC), A) SEM micrographs of cross-sectional view of SF-NGC (Magnification 23×); B) magnified section of image A (Magnification 200×); C) Side view of SF-NGC (Magnification 50×); D) fluorescent micrograph of SC cells on inner surface of SF-NGC wall.

FIG. 3 shows the results of a compression test with a custom-made test system to verify improved elasticity after modification of degummed tubular structures. Four different treatments of the initial raw scaffold were mechanically tested: sole incubation with methanol (MeOH); subsequent incubation with formic acid and methanol (FA-MeOH); subsequent incubation with $CaCl_2/H_2O$/Ethanol and methanol ($CaCl_2/H_2O$/EtOH—MeOH); subsequent incubation with $CaCl_2/H_2O$/Ethanol, formic acid, and methanol ($CaCl_2/H_2O$/EtOH—FA-MeOH).

Figure 4:
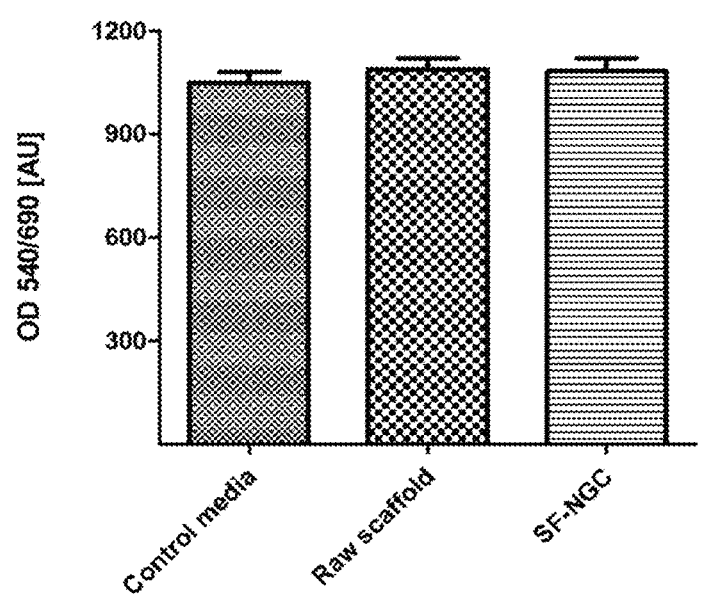

FIG. 4 shows determination of cytotoxicity by MTT assay. NIH/3T3 fibroblasts were cultured in leach-out medium of non-processed raw scaffold material and the prepared SF-NGC, respectively. Standard culture medium was used as control group. All data are means of 8 independent experiments±SEM.

Figure 5:
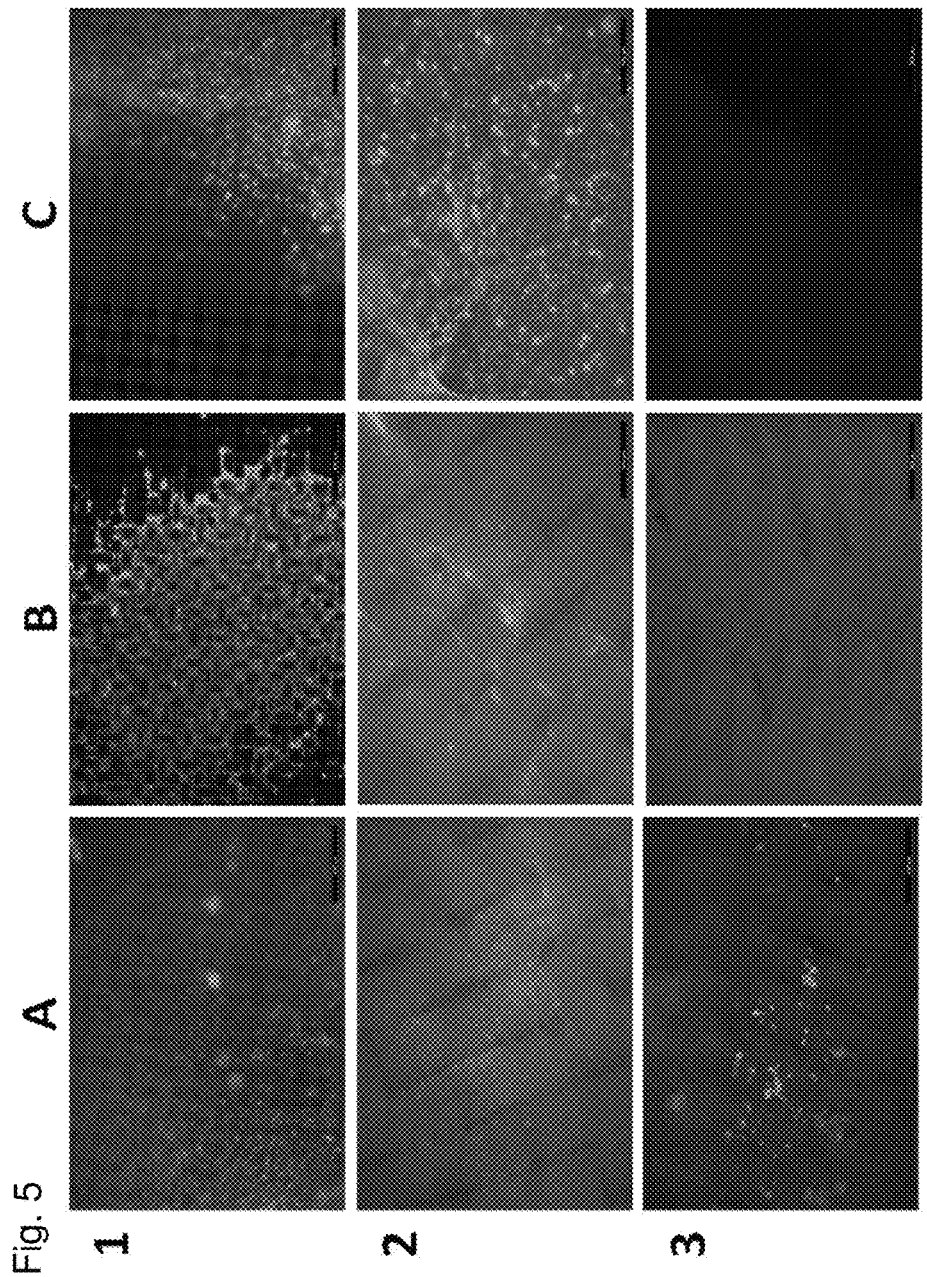

FIG. 5 shows the results of a cell permeability test via a migration assay using a fibrin clot containing NIH/3T3 fibroblasts and a second clot loaded with PDGF-AA as chemoattractant. Fibroblasts passed through different spacers, including a cell strainer mesh of 100 µm pore size (positive control, Row 1) and the unprocessed tubular silk structure (Row 2), but not through the used SF-NGC. Columns A, B, and C represent the view from the initial cell containing fibrin clot, the opposite site of the used spacer and the initial fibrin clot containing PDGF-AA, respectively. All samples were stained for residual or invaded cells via calcein AM staining.

Figure 6:
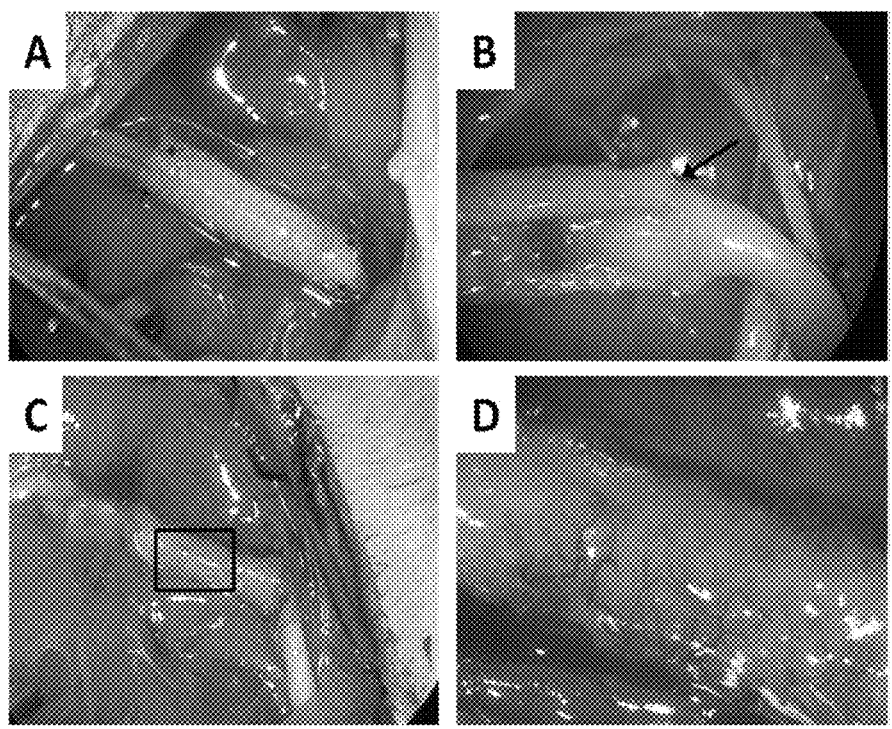

FIG. 6 shows A) silk fibroin nerve guidance conduit (SF-NGC) implanted in vivo in a rat sciatic nerve injury model. B) Proximal side of the SF-NGC as observed 1 week postimplantation. Black arrow indicates a thin layer of newly formed fibrous tissue capping the end of the SF-NGC. C) Area of peripheral nerve surgery as observed 1 week postimplantation, showing small blood vessels in the thin layer of fibrous tissue D) Magnified view of the black rectangle in C.

Figure 7:
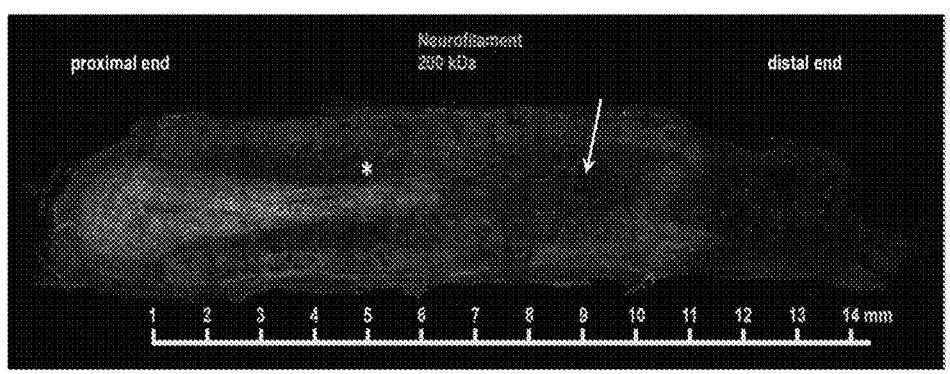

FIG. 7 shows an example of axon growth through anSF-NGC, 12 weeks postimplantation. Axons were stained via neurofilament 200 kDa immunostaining. Star and arrow indicate dense and sparse network of regenerated axons, respectively.

Figure 8:
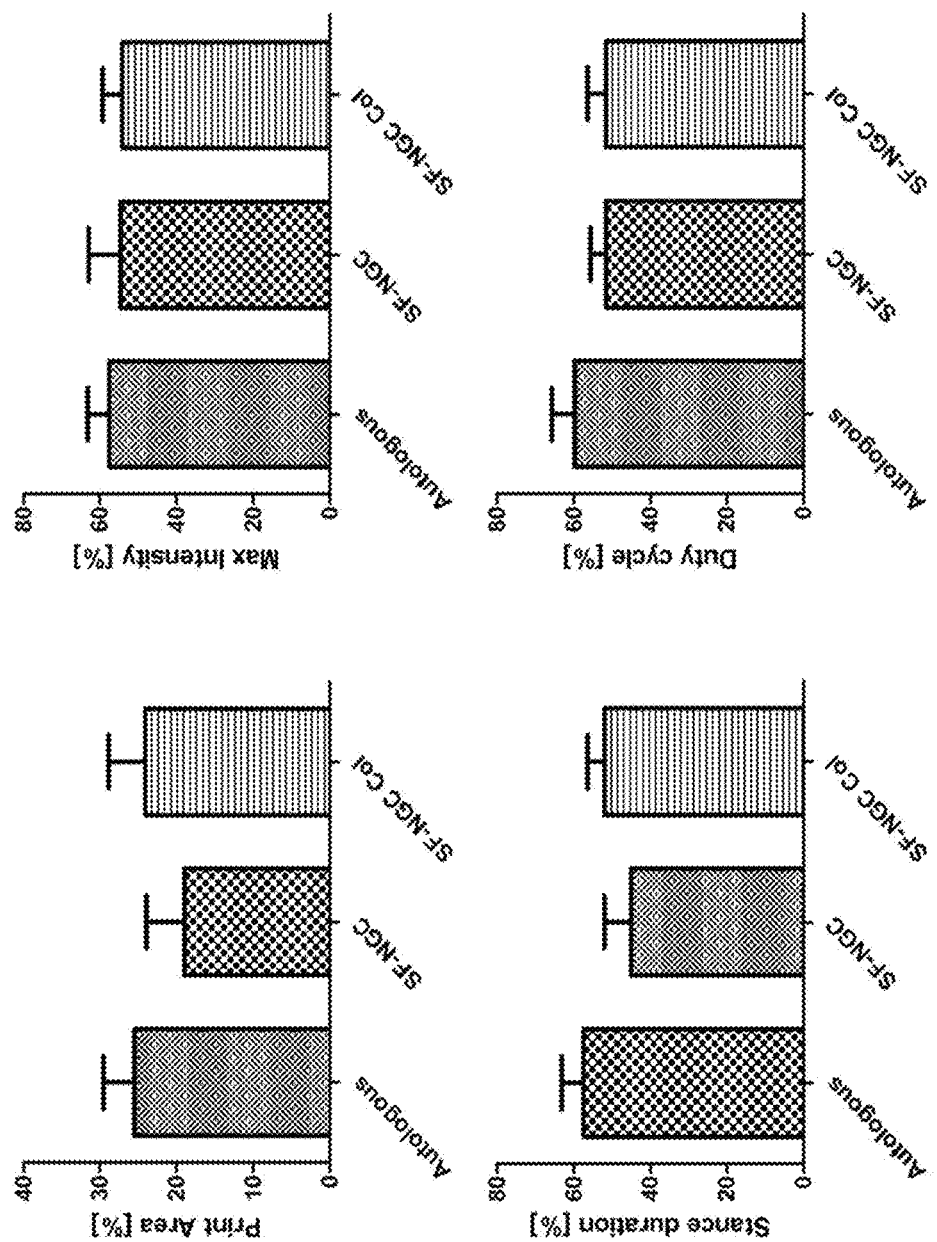

FIG. 8 shows quantitative analyses of locomotor functional recovery at 12 weeks postimplantation in animals including print area, intensity exerted at maximum floor contact area, stance duration and duty cycle of the operated right hind paw. The intensity of the right hind paw was expressed as a percentage of the contra-lateral left hind paw. All data are means of 6 animals±SD.

Figure 9:
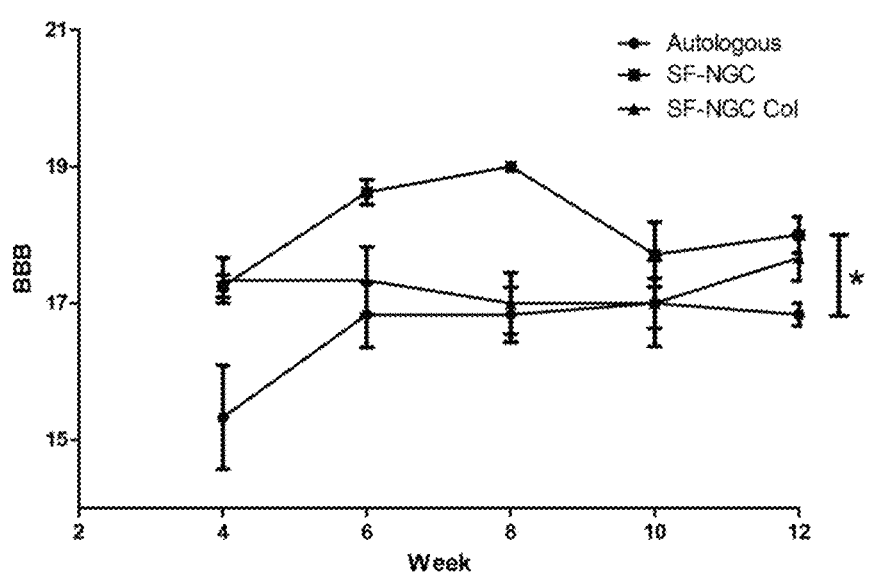

FIG. 9 shows BBB locomotor rating scale for all animals transplanted with SF-NGC, collagen-filled SF-NGC and autologous graft. All data are means of 6 animals±SD.

Figure 10:
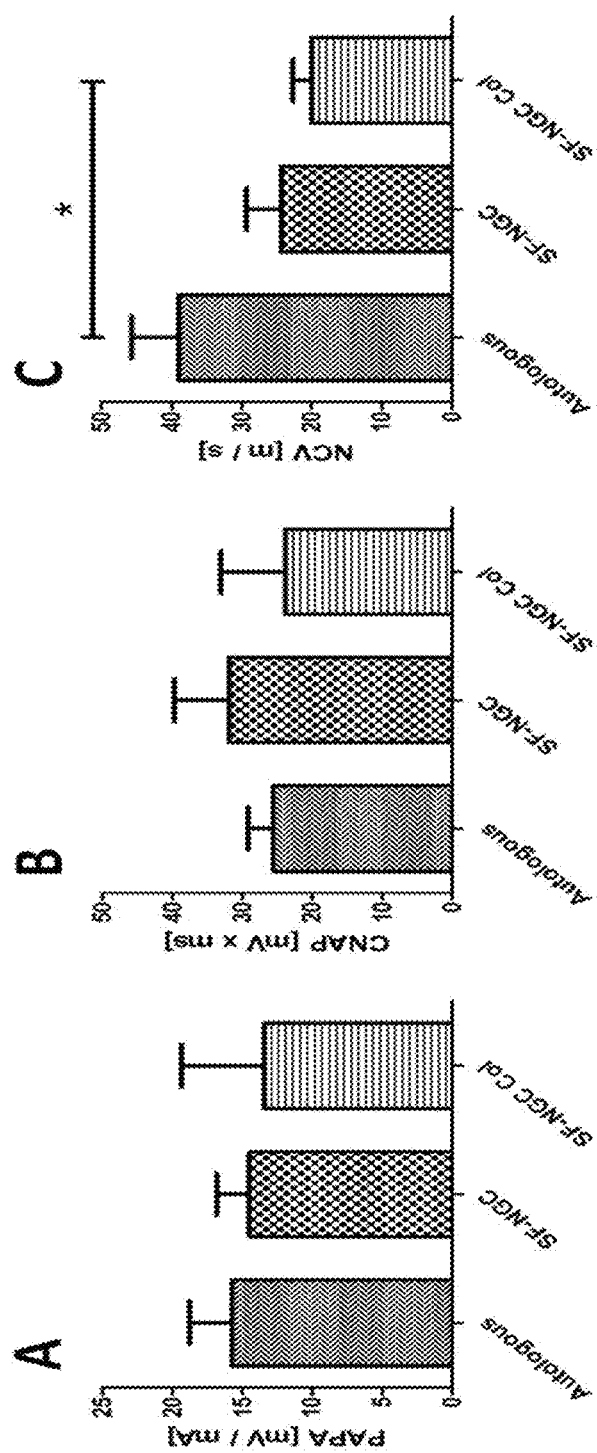

FIG. 10 shows A) electrophysiological measurements of peak action potential amplitude (PAPA), B) compound nerve action potential area (CNAP) and C) nerve conduction velocity (NCV). All parameters were determined at supramaximal stimulation. All data are means of 6 animals±SD. * indicates significant difference of $p<0.05$.

FIG. 11 shows pictures of three dimensional silk products according to the present invention which were subjected to a treatment duration of 10 or 20 sec of a $CaCl_2/EtOH/H_2O$, followed by 10 or 20 sec of formic acid treatment as described above. FIGS. 11A and 11C show the untreated silk fibroin product; FIGS. 11B and 11D show the product after treatment for 20 sec with $CaCl_2/EtOH/H_2O$, followed by 20 sec of formic acid treatment. FIG. 11E-11G show measurements of the depth of disintegration (followed by re-stabilisation) for 20 sec treatments (55.902, 73.397 and 73.662 μm); FIGS. 11H and 11I show measurements of the depth of disintegration (followed by re-stabilisation) for 10 sec treatments (17.804 and 27.57 μm).

Figure 12:
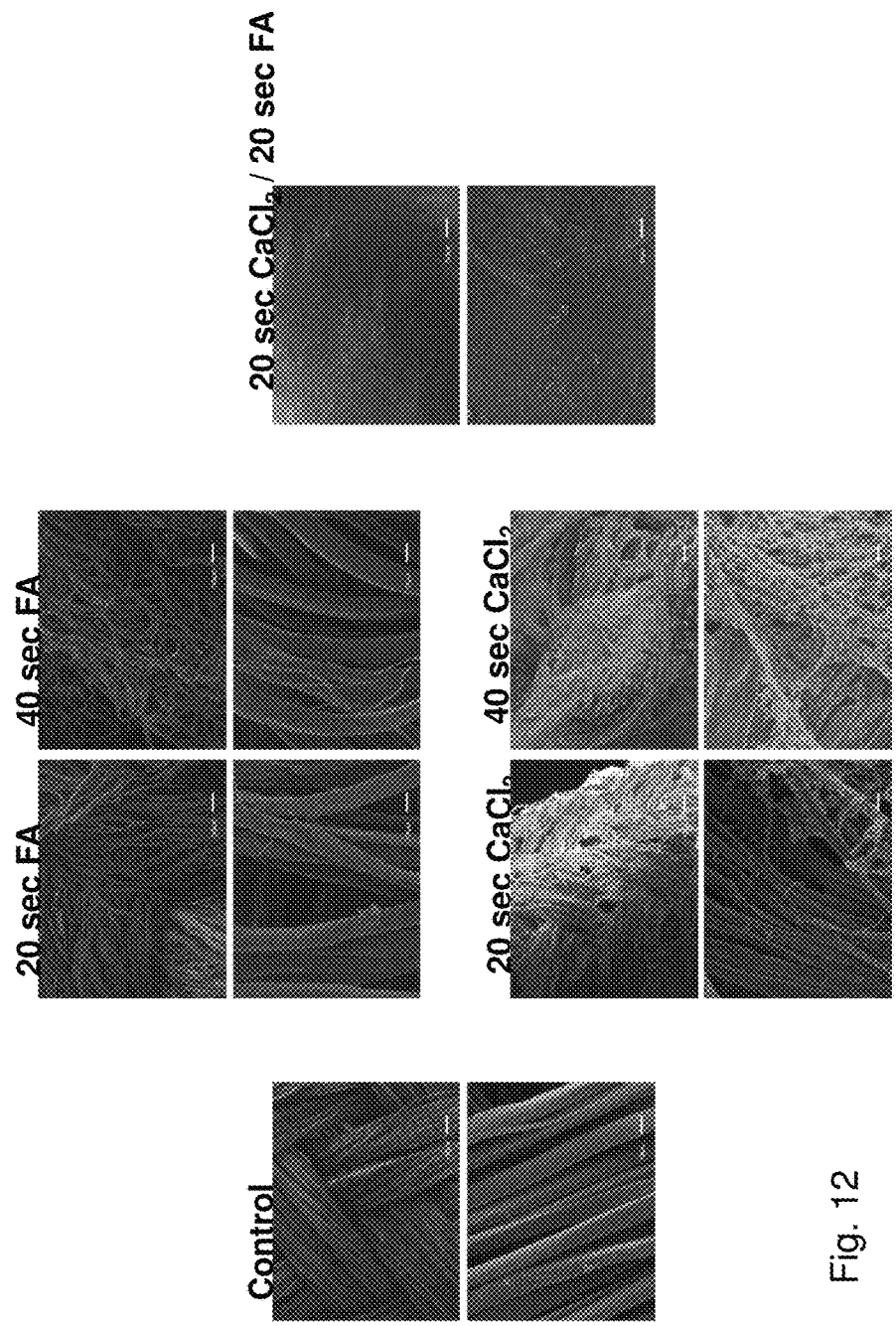

FIG. 12 shows LEFT: Scanning electron microscopy (SEM) pictures of the braided silk scaffold without treatment serving as control. MIDDLE: SEM pictures show surfaces of silk products which were subjected to a treatment of $CaCl_2/EtOH/H_2O$ (20 sec $CaCl_2$) or of formic acid (20 sec FA) for a treatment duration of 20 sec or 40 sec (40 sec $CaCl_2$; 40 sec FA). RIGHT: SEM pictures show surfaces of silk products according to the present invention which were subjected to a treatment of $CaCl_2/EtOH/H_2O$ and formic acid, each step for a treatment duration of 20 sec (20 sec $CaCl_2$/20 sec FA). Scale bars are 100 μm and 10 μm, respectively.

FIG. 13 shows welding native and undegummed silk fibers together to obtain non-disrupted and non-disintegrated structures (13A (U.S. Pat. No. 8,202,379 B1), 13B (Haverhals et al., 2010), 13C (Ghanaati et al., 2010).

EXAMPLES

Materials and Methods

Unless otherwise noted, all reagents were obtained from Sigma (Vienna, Austria) and of analytical grade.

Design and Preparation of Silk Conduits

White raw *Bombyx mori* silkworm fibers of 20/22den, 250T/m, were purchased from Textex AG (Zürich, Switzerland). The silk conduit was of tubular design and fabricated in cooperation with a commercial braiding company (Edelrid GmbH, Isny im Allgäu, Germany). Six single silk fibers form a twisted yarn, representing the raw material for the commercial braiding machines. The tubular structure is designed from six intertwined twisted yarns; illustrated in FIG. 1. The resulting raw silk conduit was degummed by boiling in 0.2 M boric acid in a 0.05 M sodium borate buffer at pH=9.0 (Jiang et al., Mat. Lett. 60 (2006), 919-925). Therefore 2 g of silk conduits were boiled two times in 500 mL of degumming solution for 45 min. After degumming, scaffolds were thoroughly washed in $ddH_2O$ and air-dried before further processing.

The degummed SF tubes were placed on an ABS (Acrylonitrile butadiene styrene) rod and dipped in a boiling solution of the ternary solvent calcium chloride/distilled water/ethanol ($CaCl_2/H_2O$/ethanol) in a molar ratio of 1:8:2 for 20 seconds. Immediately after etching the outer surface, the tubes were dipped in 100% of formic acid (FA) at room temperature for 20 seconds. The tubes were then submersed in methanol for 20 minutes and subsequently washed thoroughly with $ddH_2O$. The tubes were dried under laminar airflow and sterilized by autoclaving prior to use.

Endurance and Fatigue Tests

To test the elasticity of the SF-NGC in comparison to the unprocessed initial tubular SF-scaffold, a compression test machine was custom-made. This device was designed for repeated compression of a test specimen with constant maximum pressure. Starting from the top position, a piston is moved downwards via a servo motor (Modelcraft RS2 MG/BB standard servo, Conrad Electronic SE, Hirschau, Germany) at a speed of approximately 5 mm/s in a linear manner until it touches the probe. The piston continually stresses the probe until a predefined force threshold is reached. A force sensitive resistor (Strain gauge FSR 151, Interlink electronics, Camarillo, Calif., USA), which is integrated into the piston, works as a sensor and is part of a voltage divider. The resistance and thus the applied force is constantly sampled at 50 Hz sampling frequency using the built-in 10 bit ADC of the microcontroller (Arduino Duemilanove Controller Board with Atmega 328 μC, Atmel Munich GmbH, Garching/Munich, Germany). The system was calibrated using a laboratory scale and operates within ±5 g accuracy. Once the threshold is reached, the piston is returned to the top position, where it remains for a time set by the user. This process is repeated for the number of iterations the user set via a serial LCD display (SerLCD SFE 09395 2 line LCD Display, Sparkfun electronics, Boulder, USA).

Prior to testing, respective samples were hydrated in PBS overnight (o/n). For testing, the conduits were fixated in a Petri dish and covered with PBS. The mechanical test regimen consisted of 1,000 cycles of compression and release with 300 g load and compression duration of 300 ms per compression. After the testing procedure, tested tubes were air-dried o/n at room temperature and carefully sliced approximately 1 mm thick at the impression site for morphological analysis. Finally, deformability remaining after the compressions was assessed by SEM analysis.

SEM Analysis

Samples were fixed in 2.5% glutaraldehyde in cacodylate buffer o/n at room temperature. Then samples were dehydrated through graded ethanols followed by hexamethyldisilazane, and allowed to air-dry in a fume hood. Samples were sputter coated with Pd—Au using a Polaron SC7620 sputter coater (Quorum Technologies Ltd. East Grinstead, United Kingdom) and examined using a JEOL JSM-6510 scanning electron microscope (JEOL GmbH, Eching/Munich, Germany) at 3 kV.

Cell Culture Experiments

NIH/3T3

NIH/3T3 cell line was purchased from ECACC (European collection of cell cultures, UK). NIH/3T3 cells were cultured in DMEM containing 10% fetal calf serum (FCS) (Lonza Ltd., Basel, Switzerland) supplemented with 2 mM L-glutamine, 100 U/mL penicillin and 0.1 mg/mL streptomycin in plates coated with 0.2% gelatine solution.

Schwann-Like Cells

Adipose-derived stroma cells (ASC) were isolated from Sprague-Dawley rats and differentiated to a Schwann cell-like phenotype (Kingham et al., Exp. Neurol. 207 (2007), 267-274. Briefly, dissected visceral fat was minced and treated with collagenase type I to isolate ASC. After culturing and passaging the cells in growth medium, Modified Eagle Medium (α-MEM) containing 10% fetal calf serum (FCS; PAA, Pasching, Austria), ASCs were first incubated with growth medium containing 1 mM β-mercaptoethanol for 24 h. Then medium was replaced with fresh medium supplemented with 35 ng/mL all-trans-retinoic acid for 72 h. Finally differentiation medium containing platelet-derived growth factor (PDF; Peprotech, Vienna, Austria), 10 ng/mL basic fibroblast growth factor (bFGF; Peprotech, Vienna, Austria), 14 µM forskolin and 252 ng/mL glial growth factor 2 (GGF-2; Peprotech, Vienna, Austria) was added.

Schwann-like cells (SLCs) were seeded on the inside wall of the SF-NGC in a concentration of $10^5$ cells/mL. After two hours, cells were supplied with culture medium containing 10% FCS (PAA, Pasching, Austria), 0.1% heregulin (Preprotech, Vienna, Austria) and 14 µM forskolin. SLC attachment to the inner wall structure of the SF-NGC was evaluated after three days with Calcein AM staining (Invitrogen, Vienna, Austria).

Cell Permeability

A cell migration assay was designed to verify the cell impermeability of the SF-NGC. A 100 µl fibrin clot (Tisseel, Baxter, Vienna, Austria) containing PDGF-AA (Peprotech, Vienna, Austria) was used to induce cell migration. 10 ng of PDGF-AA was mixed thoroughly in fibrinogen prior to the induction of polymerization with 250 Units/mL thrombin. The resulting tight fibrin structure avoids burst release of PDGF-AA. This fibrin clot was then placed inside the investigated tubes and the so-assembled constructs were pinned in silicone-coated (Sylgard® 184, Dow Corning Europe S.A., Seneffe, Belgium) 12-well plates. A second 100 µl fibrin clot containing $2.5 \times 10^5$ NIH/3T3 fibroblasts was placed on top of the tube. Fibrinogen was polymerized with 2 Units/mL thrombin to create a loose and homogenous fibrin structure and to allow fibroblasts to migrate from the clot towards chemotactic stimulus. As positive control, the fibrin clot with cells was separated from the clot containing PDGF-AA using a nylon mesh of a cell strainer with 100 µm pore size. (Becton Dickinson, Schwechat, Austria). Medium was added until constructs were completely covered and changed on days 2 and 4 after assembling the assays. On day 6, cell migration was evaluated by staining the fibrin clot containing PDGF-AA with calcein AM (Invitrogen, Vienna, Austria). Besides the possibility of fixing the constructs to a Petri dish, Sylgard® 184 is known to discourage cell adhesion as a result of its hydrophobic character (Ai et al., Cell Biochem Biophys. 38 (2003), 103-114) and therefore avoids the possibility of cell migration from one clot to the other over the surface of the cell culture plate. As a result, the only way to move from one clot to the other is to pass through the SF-NGC and therefore a certain cell permeability of the SF-NGC would be required.

Cytotoxicity Assay

To test cytotoxicity of the prepared SF-NGC, 1 g of dissected material of SF-NGC was immersed in 5 mL cell culture medium for at least 24 h. In parallel, $0.2 \times 10^5$ NIH/3T3 fibroblasts per well were seeded into 24-well plates. Then the media containing leach-out products from the dissected material was filtered (0.22 µm, Rotilabo, Karlsruhe, Germany) and used to change media in the cell cultures. Standard culture medium was used as negative control. Cell culture medium was aspirated and respective cell culture medium containing 650 mg/mL MTT [3-(4,5-dimethylthiazol-2-yl)-2,5-diphenyltetrazolium] bromide was added to each well. After 1 h of incubation at 37° C. and 5% $CO_2$, medium was aspirated and MTT formazan precipitate was dissolved in DMSO by shaking mechanically in the dark for 20 min. Aliquots of 100 µl of each sample were transferred to 96-well plates. The absorbance at 540 nm was read immediately on an automatic microplate reader (Spectra Thermo, TECAN Austria GmbH, Austria). Optical density (OD) values were corrected for unspecific background.

Animals and 10 mm Nerve Defect Model

All animals were housed in the facilities of the Ludwig Boltzmann Institute for experimental and clinical Traumatology in a temperature-controlled environment. Animals were given food and water ad libitum. All experimental protocols were approved by the City Government of Vienna, Austria in accordance with the Guide for the Care and Use of Laboratory Animals as defined by the National Institute of Health.

A total of 22 female Sprague-Dawley rats (Animal Research Laboratories, Himberg, Austria), weighing between 350-450 g were used in the experiments. 18 animals were randomly assigned into three different treatment groups: autologous grafting (n=6), SF-NGC (n=6) and collagen-filled SF-NGC (n=6) for 12 weeks observation. The animals were weighed and anesthetized in a fume box with 3.5% isoflurane (Forane®, Abbott, Vienna, Austria) at a flow rate of 800 mL/min. Subsequent anesthesia throughout the surgical procedure was maintained using 2.5% isoflurane via a nosepiece. At right mid-thigh level, the surgical area was shaved and cleaned with β-Isodona (Mundipharma, Vienna, Austria). All the following surgical procedures were carried out under an operating microscope (Leica M651, Leica GmbH, Vienna, Austria). The sciatic nerve was exposed by incision of the skin and muscle. An 8 mm segment of the sciatic nerve was excised resulting in a 10 mm gap after the slight retraction of the distal and proximal stumps. In the autologous grafting group, an 8 mm segment of the sciatic nerve was excised, flipped 180°, and then sutured back to the proximal and distal stumps using Ethilon 8/0 (Ethicon-Johnson & Johnson, Brussels, Belgium) through the epineurium. In both SF-NGC groups, the conduit was implanted by insertion of the proximal and distal nerve stumps into the 12 mm tube and coaptated to the scaffold by two epineural sutures. In one group the lumen of the SF-NGCs were additionally filled with collagen type I from rat tail origin (Millipore, Vienna, Austria). Afterwards the muscle layers were sutured with continuous running suture (Vicryl 4/0, Ethicon-Johnson & Johnson, Brussels, Belgium) and the skin closed by single resorbable stitches (Vicryl 4/0, Ethicon-Johnson & Johnson, Brussels, Belgium). Subsequently, the animals were placed back in their cages for recovery. Analgesia treatment of 0.75 mg/kg BW Meloxicam (Metacam®, Boehringer Ingelheim, Ingelheim/Rhein, Germany) and 1.25 mg/kg BW butorphanol (Butamidor®, Richter Pharma AG, Wels, Austria) was given immediately before the surgical procedure and for two days thereafter.

To obtain initial information on the behavior of the SF-NGCs and reactions from the surrounding tissue in vivo, a study with short implantation time points of 1 and 3 weeks (2 animals/timepoint) was carried out according to the surgical procedure described above.

Sampling of Tissue, Perfusion and Immunohistochemistry

Respectively after 1, 3 or 12 weeks after surgery, the animals were deeply anesthetized by inhalation of 3.5% isoflurane and euthanized with 110 mg/kg BW ketaminhydrochlorid (Ketasol®; Dr. E. Graeub AG, Berne, Suisse) and 12 mg/kg BW xylazin (Rompun® 2%, Bayer AG, Vienna, Austria) intraperitoneally. Via the ascending aorta, animals were perfused with 4% paraformaldehyde in 0.1 M phosphate buffer at pH 7.4. Then the autologous transplant or the implanted SF-NGC were harvested under operating microscope along with the proximal and distal nerve stump.

To indicate axon regeneration via immunohistochemistry staining a mouse primary antibody: anti-neurofilament 200 kD (Abcam Ltd., Cambridge, UK) was used (Huang et al., Biomat. 33 (2011), 59-71; Huang et al., Eur. J. Neurosci. 23 (2006), 273-278).

Behavioral Tests—Gait Analysis (CATWALK™)

To verify the functional recovery progress of the test animals the Catwalk (Noldus, Wageningen, Netherlands) footprint analysis system was used. This method allows an objective quantification of multiple static and dynamic gait parameters (Deumens et al., J. Neurosci. Meth. 163 (2007), 120-130; Bozkurt et al., J. Neurosci. Meth. 173 (2008), 91-98). Pre-training with the animals was performed for 3 weeks before surgery. After the procedure the animals were tested once a week and up to 12 weeks for all groups. During each run, a video camera positioned underneath the glass plate captures the actual footprints. With this analysis differences between positions, dynamics, and pressure of each footstep can be detected. Various parameters for locomotor functional recovery were determined including print area, the total contact area by the paw during walking, maximum intensity, the exerted pressure at the moment of maximum glass floor contact of the paw, stance duration, time of contact of the paw with the glass floor, and duty cycle, division of stance duration and the sum of stance duration plus the time that the paw is not in contact with the glass floor. The intensity of the right hind paw was expressed as a percentage of the contra-lateral left hind paw. The Catwalk experiment was performed in a blinded fashion.

BBB Test

The Basso, Beattie and Bresnahan (BBB) test was originally designed to assess locomotor functional recovery after contusion injuries in rat spinal cord. Scores range from complete paralysis (0) up to normal locomotion (21). Here, the BBB score was used as an evaluation parameter for peripheral nerve recovery as previously described (Schmidhammer et al., Acta Neurochir. 100 (2007), Supplement 161-167) and was performed by three experienced reviewers "blind" to the animals' identities.

Electrophysiology and Histology:

weeks postimplantation, electrophysiological analysis (NeuroMax; XLTEK, Oakville, Ontario, Canada) was carried out as previously described (Schmidhammer et al., J. Trauma 56 (2004), 571-584) and included the peak action potential amplitude, the compound action potential area (CNAP) and the nerve conduction velocity.

Statistical Analysis

Statistical analysis was performed with the statistics software Graph Pad Prism (Graph Pad Software Inc., San Diego, Calif., USA). Normal distribution of data was tested with the Kolmogorov-Smirnov test. Functional recovery data obtained via Catwalk gait analysis and BBB score, MTT and electrophysiological data was analyzed with one-way ANOVA. All graphs in this study are shown as mean±standard deviation (SD).

Results

Preparation and Topography of Silk Conduits

As depicted in FIG. 1, the raw SF-NGC consists of a braided design composed of single silk fibers. After degumming the surface, the SF-NGC was subsequently etched with $CaCl_2/H_2O$/Ethanol and FA for 20 seconds each, fixating its' structure with methanol. Topographically, these treatments result in a fusion of the outer single silk fibers to a closed layer with a thickness ranging from about 25 to 75 μm (FIG. 2A, B). In contrast to the outer wall, where single silk fibers appear fused and form a smooth layer (FIG. 2C), the wall side facing the inner lumen still represents the braided structure of single silk fibers. FIG. 2D shows that these inner single silk fibers serve as a good substratum for SC cells and cause a directed cell alignment due to their braiding design.

Endurance Test

To verify the requested elasticity of the SF-NGC in order to withstand external pressure from surrounding tissue which could negatively lead to a collapse of the tubular structure, mechanical endurance tests were performed with a custom-made system. Scaffolds were compressed for 1,000 cycles with 300 g per compression and a pressure duration of 300 ms. In all treatments the SF-NGCs were incubated with methanol in a final step to fixate the modified structure of the scaffolds. Unprocessed or FA-treated SF-NGCs showed a severe collapse after mechanical loading (FIG. 3). $CaCl_2/H_2O$/ethanol treatment improved the mechanical resistance of the SF-NGCs resulting in preservation of some lumen but substantial deformation was still present. None of these three treatments was able to provide the SF-NGC with elastic properties to withstand external pressure. However, the SF-NGCs treated with $CaCl_2/H_2O$/ethanol followed by FA were able to retain their round shape after testing.

Cytotoxicity Assay

MTT assay was employed to investigate the content of possible cytotoxic residuals, originating from the preparation process in the generated SF-NGC. Dissected material from the SF-NGC and the unprocessed raw silk scaffold was leached out with cell media. These leach-out media were used as culture media for 24 h. According to the results of the MTT assay (FIG. 4), no significant difference in cell viability of NIH/3T3 fibroblasts between untreated standard cell culture medium, leach-out media of raw scaffold or SF-NGC material could be detected, indicating the non-cytotoxicity of the prepared SF-NGC.

Cell Permeability

A cell migration assay to verify cell impermeability of the SF-NGC was designed, based on the chemotactic properties of PDGF-AA on fibroblasts to induce cell migration from a cell-carrying fibrin clot to another fibrin clot that contains PDGF-AA. To invade the fibrin clot containing PDGF-AA, NIH/3T3 fibroblasts have to pass through either a cell strainer with 100 μm pore size (positive control group), an unprocessed raw tubular silk scaffold, or an SF-NGC. Significant fibroblast migration was observed by PDGF-AA stimulation for 5 days through the mesh of a cell strainer (FIG. 5, Row 1) and the raw scaffold (FIG. 5, Row 2), but not through the SF-NGC (FIG. 5, Row 3).

Preliminary In Vivo Results

Preliminary in vivo studies were carried out to evaluate tissue biocompatibility of the implanted SF-NGC. FIG. 6A shows the proximal and distal nerve stumps coaptated to the SF-NGC by two epineural sutures. After 1 week postimplantation, visual inspection revealed that the SF-NGC did not exhibit substantial degradation (FIG. 6B). Furthermore, no signs of inflammatory reactions or the neuroma formation at the coaptation sites could be detected. The entire surface of the implanted graft was covered by a thin layer of fibrous tissue. Interestingly, the proximal as well as the distal end of the transplanted SF-NGC was capped by the fibrous tissue, leading macroscopically to an interface between the scaffold material and the nerve stumps (FIG. 6B). Moreover, this thin layer of fibrous tissue showed small blood vessels (FIG. 6C, D).

Axon Regeneration

The present results showed that a short gap of 8 mm in the rat sciatic nerve could be bridged by implanting an SF-NGC into the defect site. Revealed using neurofilament 200 staining, FIG. 5 shows the distribution of regenerated axons throughout the lumen of the implanted SF-NGC. From the proximal to the distal end, a regeneration process of axons is clearly visible (FIG. 5, indicated by *), decreasing after approximately 6.5 mm. Despite this diminishment of axon density, a bundle of regenerated axons can still be seen, reaching the distal stump 12 weeks postimplantation. The filling of the lumen with collagen did not affect axon regeneration.

Functional Recovery—Catwalk

At 12 weeks postimplantation, the mean print area of the operated right hind paws was comparable between the autologous control and the collagen-filled SF-NGC group. The mean print area of the SF-NGC without collagen group was lower than both autologous control and collagen-filled SF-NGC groups, but not significantly different. The mean intensity exerted by the right hind paws showed similar results between both SF-NGC groups, but were not significantly reduced compared to the autologous control. Mean stance duration of the right hind paws indicate an improvement of functional recovery when the SF-NGC is filled with collagen compared to the pure SF-NGC, but was not of statistical significance. Similar to the mean intensity, the mean duty cycle of the right hind paws did not differ between the collagen-filled SF-NGC and the SF-NGC group, but the respective mean values were lower than that for the autologous control.

TABLE 1

Quantitative analyses of locomotor functional recovery at 12 weeks postimplantation in animals including print areas, intensity exerted at maximum floor contact area, stance duration and duty cycle of the operated right hind paw. The intensity of the right hind paw was expressed as a percentage of the contralateral left hind paw. All data are means of 6 animals ± SD.

|  | Autologous | SF-NGC | SF-NGC Col |
| --- | --- | --- | --- |
| Print Area of the right hind paw | 25.5 ± 9.9 | 19.0 ± 12.2 | 24.1 ± 11.6 |
| Intensity exerted by the right hind paw | 57.6 ± 13.7 | 54.6 ± 20.5 | 54.2 ± 12.4 |
| Stance duration | 57.5 ± 14.0 | 45.1 ± 17.2 | 52.1 ± 11.0 |
| Duty cycle | 59.8 ± 14.5 | 51.7 ± 9.5 | 51.7 ± 11.7 |

BBB Recovery Scale

BBB scores were determined 4, 6, 8, 10 and 12 weeks postimplantation. FIG. 8 illustrates the recovery of nerve function from week 4 to week 12 after surgical intervention.

In the first postoperative evaluation (4 weeks), the toe clearance during forward limb advancement of the animals transplanted with SF-NGCs with or without collagen occurred more frequently than those of the animals treated with autologous grafts. At 8 weeks postimplantation, the mean BBB score for the sole SF-NGC group was significantly higher than the autologous as well as the collagen-filled SF-NGC groups. At the last postoperative evaluation timepoint (12 weeks), animals with autologous grafting demonstrated a lower BBB score than animals transplanted with SF-NGC, with or without collagen. At 12 weeks, an improvement of the BBB score for the animals receiving SF-NGC constructs as a result of the tubular filling with collagen could not be detected.

Electrophysiology 12 weeks postimplantation, electrophysiological studies were carried out determining three different parameters; peak action potential amplitude (PAPA), compound nerve action potential area (CNAP) and nerve conduction velocity (NCV). The results are summarized in Table 2 and illustrated in FIG. 9. No significant differences for PAPA and CNAP between SF-NGC, collagen-filled SF-NGC and the autologous control could be determined. In contrast, the NCV values of the autologous group were significantly higher compared to the both SF-NGC groups, with or without collagen.

TABLE 2

Electrophysiological measurements of peak action potential amplitude, compound nerve action potential area and nerve conduction velocity. All parameters were determined at supramaximal stimulation. All data are means of 6 animals ± SD.

|  | Autologous | SF-NGC | SF-NGC Col |
| --- | --- | --- | --- |
| Compound nerve action potential area [mV/mA] | 25.7 ± 8.8 | 32.0 ± 19.1 | 23.8 ± 20.8 |
| Peak action potential amplitude [mV × ms] | 15.8 ± 7.4 | 14.5 ± 5.7 | 13.5 ± 13.2 |
| Nerve conduction velocity [m/s] | 39.0 ± 16.3 | 24.3 ± 11.3 | 20.0 ± 6.0 |

Treatment Duration and Depth of Disintegration

Figure 11A:
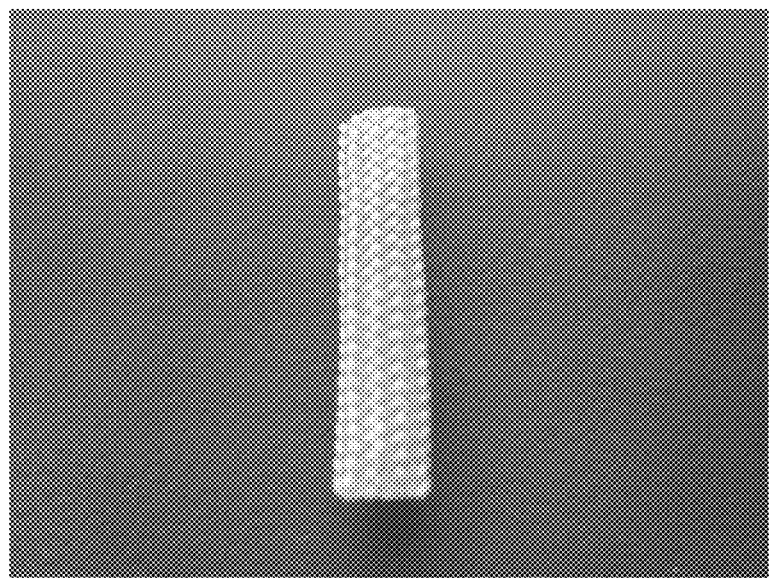
Figure 11B:
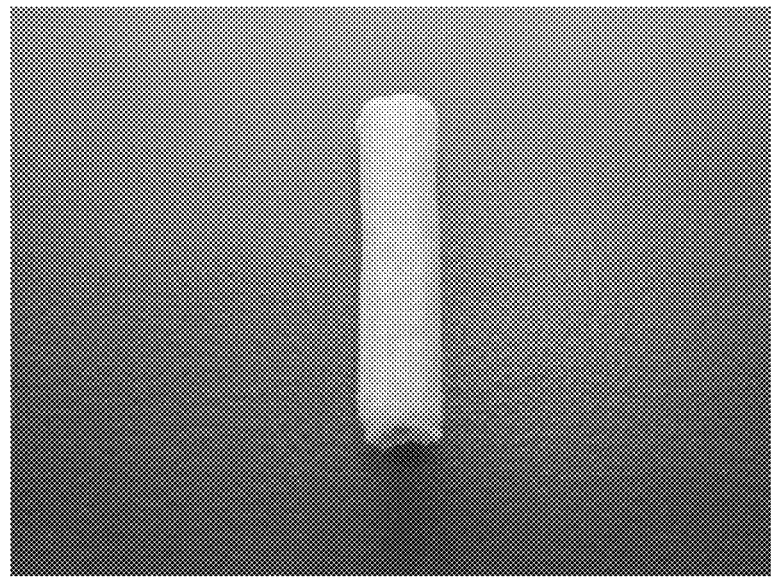
Figure 11C:
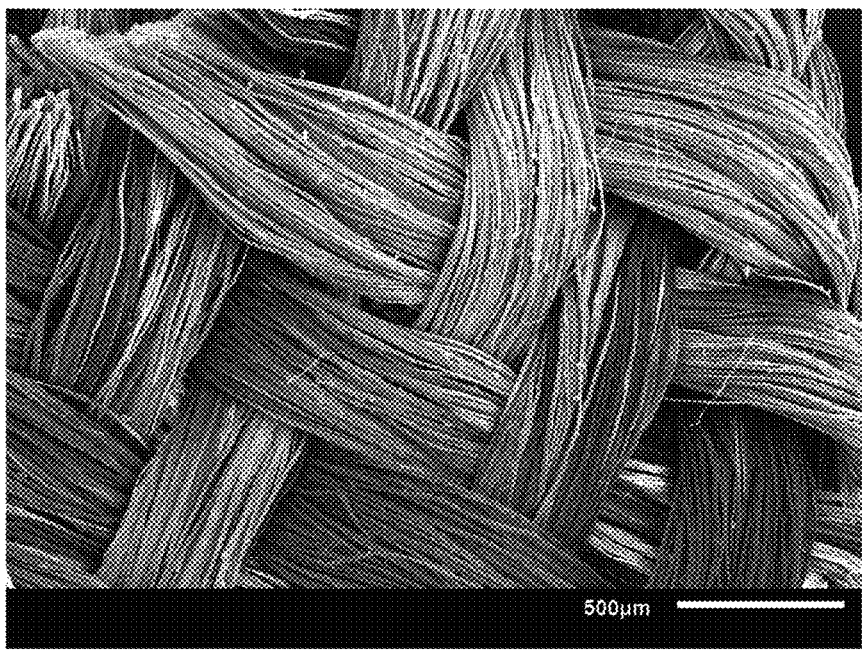
Figure 11D:
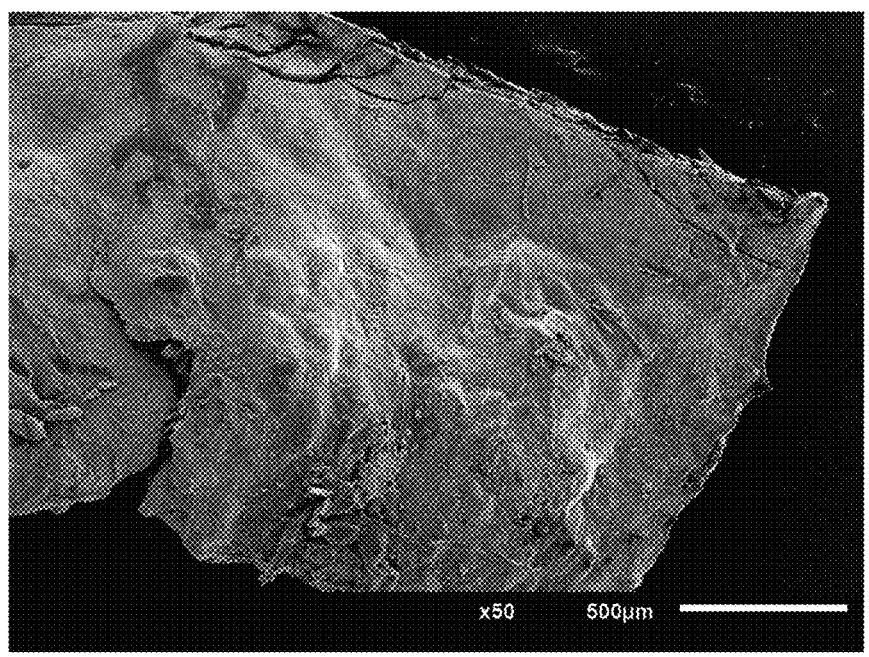
Figure 11E:
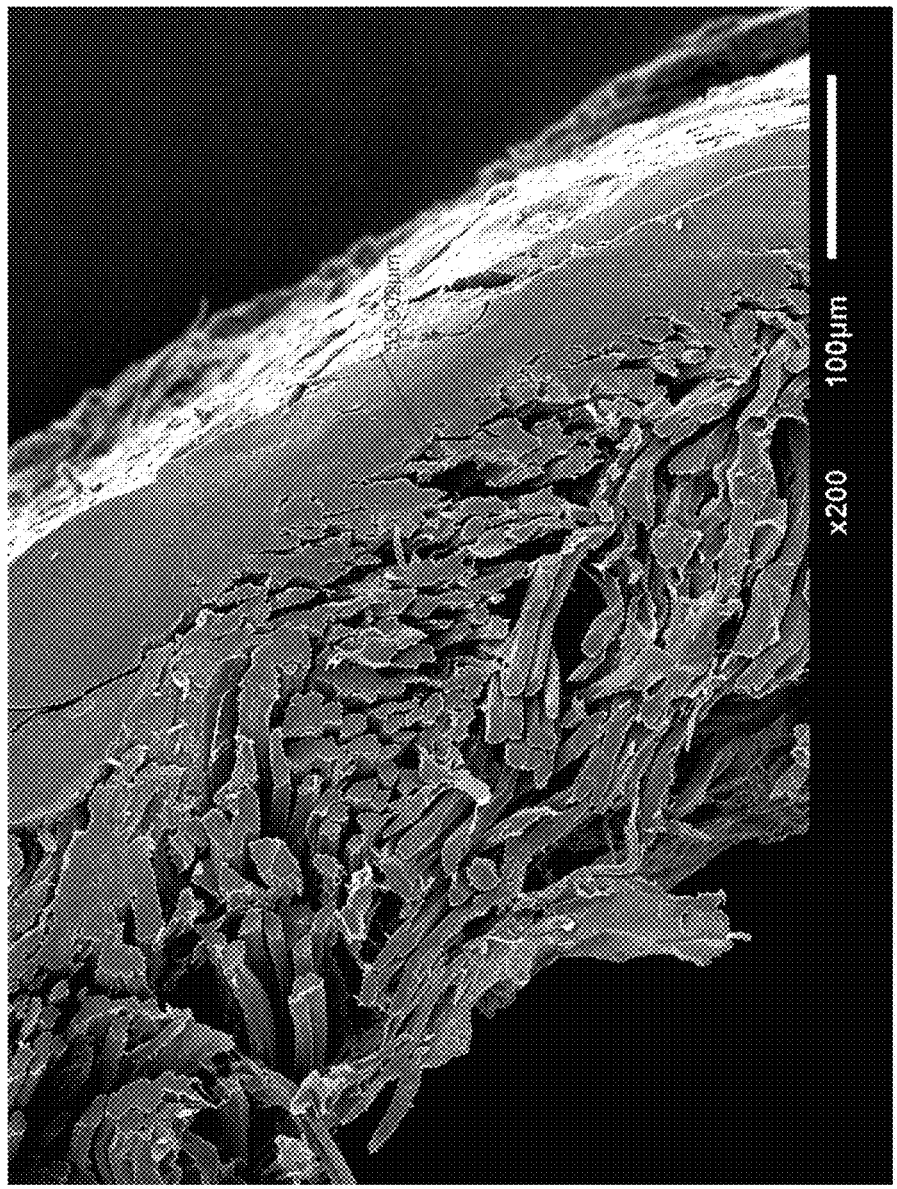
Figure 11F:
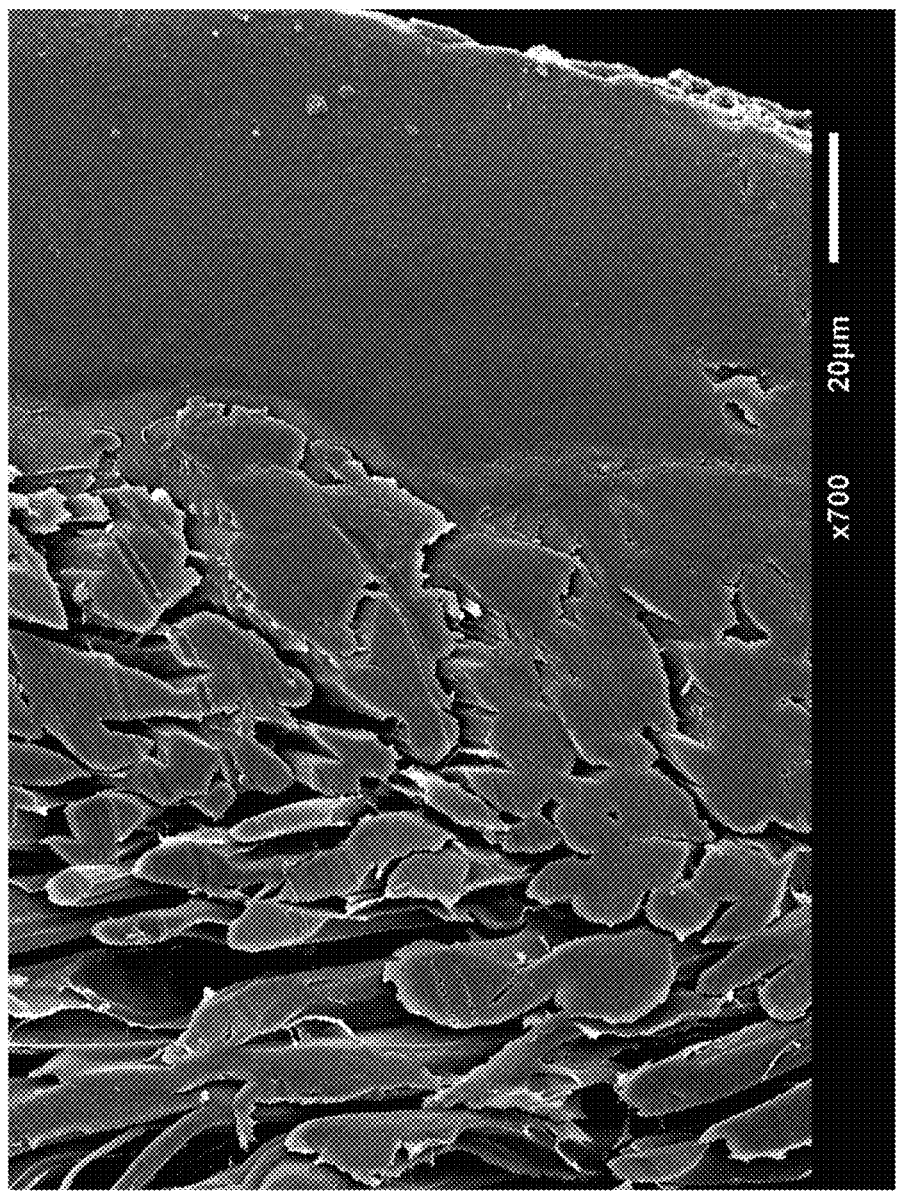
Figure 11G:
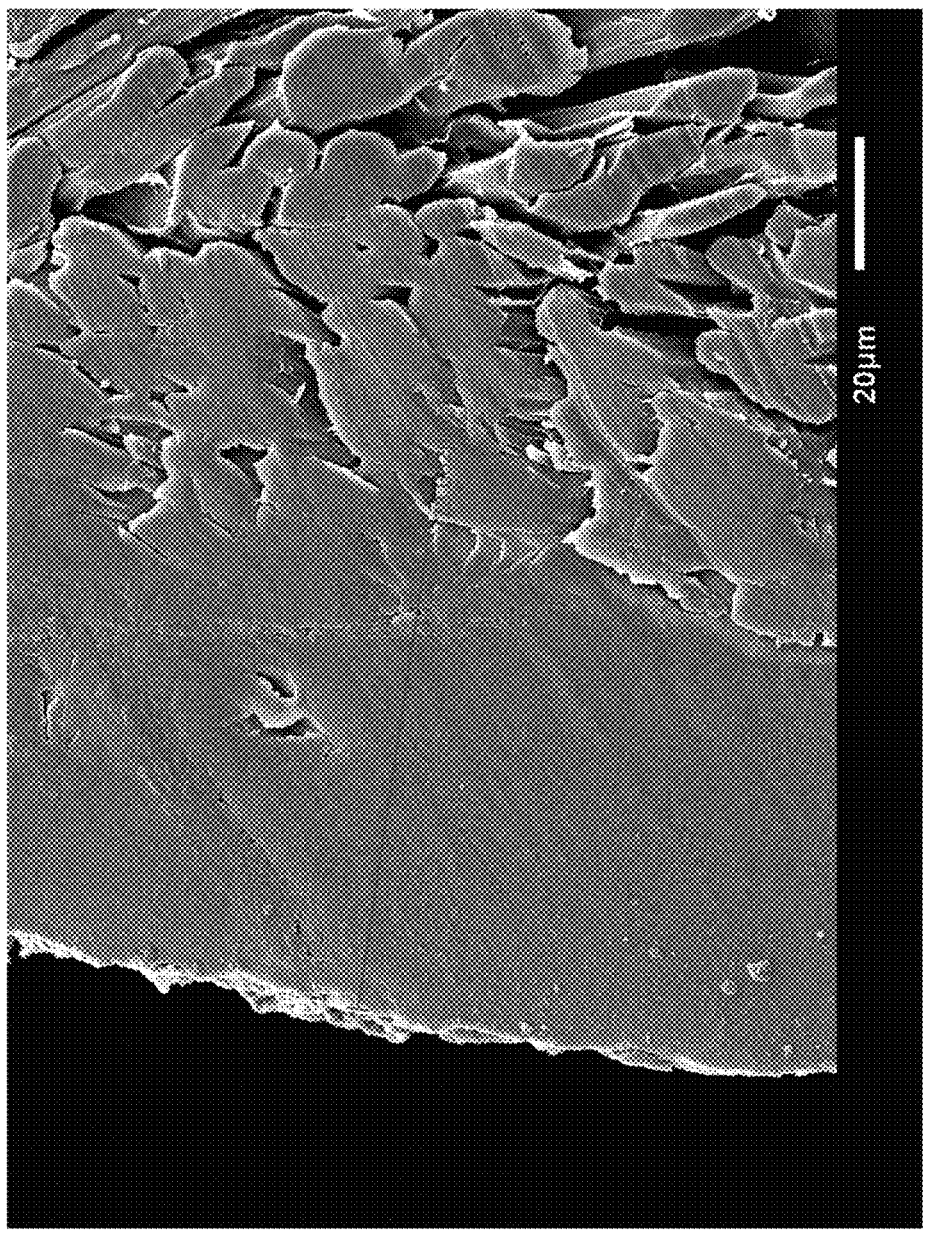
Figure 11H:
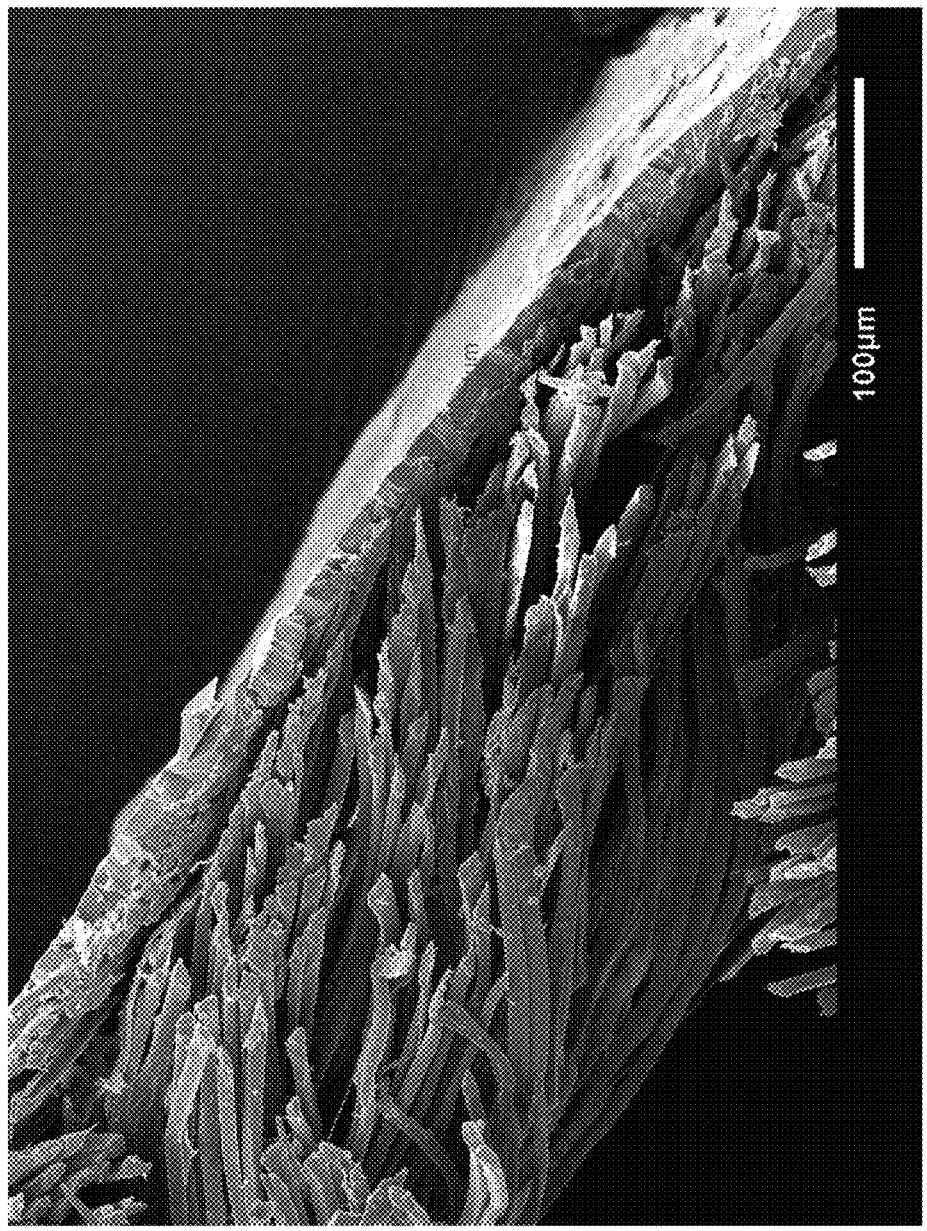
Figure 11I:
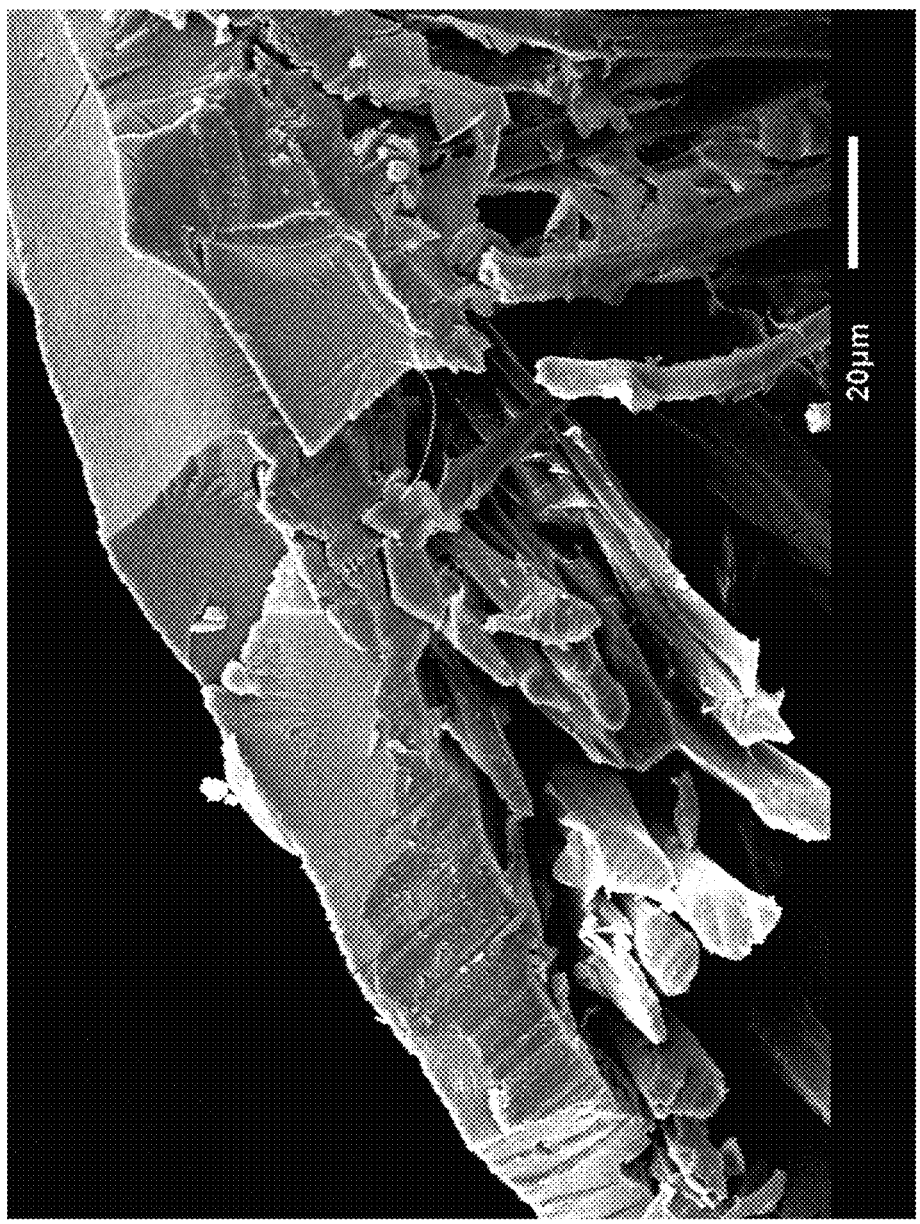

Depth of disintegration can be easily controlled and managed by control of the treatment duration. A three dimensional silk product according to the present invention was subjected to a treatment duration of 10 or 20 sec of a $CaCl_2/EtOH/H_2O$, followed by 10 or 20 sec of formic acid treatment as described above. The results are depicted in FIG. 11: FIGS. 11A and 11C show the untreated silk fibroin product; FIGS. 11B and 11D show the product after treatment for 20 sec with $CaCl_2/EtOH/H_2O$, followed by 20 sec of formic acid treatment. FIG. 11E-11G show measurements of the depth of disintegration (followed by re-stabilisation) for 20 sec treatments (55.902, 73.397 and 73.662 µm); FIGS. 11H and 11I show measurements of the depth of disintegration (followed by re-stabilisation) for 10 sec treatments (17.804 and 27.57 µm).

Discussion

In this study a braided tubular structure of silk fibroin (SF) fibers served as raw material for the production of a nerve guidance conduit (NGC). Through subsequent chemical treatment of the textile engineered tubular SF structure a conduit exhibiting topographical anisotropy and mechanical properties was generated that favor its use as a NGC.

Elasticity and resistance to kinking of the SF tubes was enhanced by a chemical treatment with ternary solvent CaCl$_2$/H$_2$O/ethanol (1:2:8 mole ratio), FA (as a re-stabilising agent according to the present invention) and methanol (FIG. 2). CaCl$_2$/H$_2$O/ethanol dissolve the native SF fibers, while methanol induces crystallinity by forming β-sheets. In this context, FA was described to induce an ordered structure/molecular arrangement in the solution state that results in a β-sheet conformation upon eliminating the dissolving FA. This unique property of FA was used to generate a crystalline-like outer layer of the nerve conduit wall (FIG. 2). Furthermore, by varying incubation time with preparation reagents, the thickness of the outer crystalline layer can be controlled. This preparation process leads to SF scaffolds for various tissue engineering (TE) and regenerative medicine approaches such as enhancing vascularization or wound dressings.

Thanks to the CaCl$_2$/H$_2$O/ethanol treatment elasticity and resistance to kinking of the SF-NGC were remarkably increased. Revealed by endurance tests performed with a custom-made test system (FIG. 1), these improved mechanical properties enable the SF-NGC to withstand external compression forces from surrounding tissue (FIG. 3).

Prior to implantation, biocompatibility assays with the prepared SF-NGC were performed. For in vitro cell toxicity testing a common MTT assay (FIG. 4) was used indicating that no substances were released from the material, which could affect cell viability negatively. Moreover, the use of the inner side of the SF-NGC as a cell substratum for SLCs was evaluated (FIG. 2 D). In general, Schwann cells are regarded the most important factor in peripheral nerve regeneration, due to their initial proliferation through the nerve channel, enabling axons to sprout and to elongate thereafter. Therefore, the prevailing idea in peripheral nerve TE is to test potential peripheral nerve regeneration biomaterials with Schwann cells or SLCs. In the present examples, SLCs differentiated from adipose derived stem cells showed good seeding and attachment capabilities on the investigated SF-NGC material comparable to tissue culture polystyrene.

Furthermore, the in vitro testing included a cell permeability analysis. A migration assay evaluated cell infiltration from the outside into the lumen of the SF-NGC. It was demonstrated that fibroblasts were able to transverse the mesh of a cell strainer with a 100 μm pore size as well as a raw unprocessed silk scaffold, but not SF-NGC, intended for implantation. This is a crucial finding as in vivo, cells from surrounding tissue, especially fibroblasts, should not be able to migrate into the gap between two nerve stumps. Invading cells would then form fibrous tissue that would sterically block a growing nerve.

Interestingly, apart from its role as an SF solving and crystallization agent, FA can be used to modify in vivo vascularization. It was demonstrated that by varying treatment time with FA, the in vivo vascularization of SF-based 3D non-woven micronets could be controlled. In the present preliminary studies on in vivo biocompatibility of SF-NGC, in addition to the absence of severe signs of inflammation, a thin layer of fibrous tissue containing small blood vessels was documented (FIG. 6C, D). These observations showed microvascular growth into the SF-NGC, possibly triggered by the release of growth factors from the regenerating nerve and serving as a nutrition supply for the regenerating nerve. This microvascular growth into the SF-NGC could be influenced by the FA treatment during preparation. Another interesting aspect of the formed layer of fibrous tissue was that it capped the ends of the graft, forming a gradual interface between nerve stumps and the implanted SF-NGC. This gradual interface could prevent sliding of the implanted SF-NGC that would have led to further nerve damage, including neuroma formation.

Longitudinal-sections of the regenerated nerve tissues, 12 weeks after implantation of a SF-NGC, showed complete bridging of a 10 mm ischiadic nerve defect by regenerated axons (FIG. 7). However, it has to be noted that the bundled axons are much denser in the first 65% out of the entire defect size. The regeneration capacity of axons could be limited and they could be in need of further nerve growth stimulating factors such as neurotrophic factors, an a lumen filling extracellular matrix or SLCs.

The present examples also show the in vitro and in vivo evaluation of the SF-NGC presented. For In vivo testing one group with collagen located inside the lumen of the conduits was included. The use of luminal fillers is of emerging interest in the field of artificial nerve conduits, especially when facing longer, so-called critical sized, gaps. In addition to its appraisal in literature thanks to its assisting role in nerve regeneration, a beneficial effect of collagen on peripheral nerve regeneration has been observed. Moreover, collagen is regarded a carrier matrix for the delivery of growth factors and cells to a nerve defect site. Nevertheless, in the present examples, no beneficial effects of collagen as a luminal filler were observed in either histologic analysis or in locomotor function recovery. Electrophysiological measurements even indicated a significant reduction of nerve conduction velocity in the collagen-filled SF-NGC group compared to the autologous control group (FIG. 9C).

Walking track analysis (Catwalk) for the assessment of functional recovery did not reveal any differences between SF-NGC, collagen-filled SF-NGC and autologous controls 12 weeks post implantation. Catwalk results are consistent with a recent study in which conduits were also fabricated from *Bombyx mori* silk but contained a luminal fibrous filling of Spidrex®, another a silk-based biomaterial.

Apart from walking track analysis, locomotor function recovery was evaluated via the BBB scale method. This scale method was originally used to assess function recovery and locomotion in spinal cord injury models, but it is also suited to evaluate functional recovery in nerve defect models. The BBB score was considered to be more sensitive in detecting residual deficits than the traditionally used sciatic functional index (SFI). In the present examples the bridging of the nerve defect via SF-NGC and collagen-filled SF-NGC grafting led to significantly superior functional recovery in BBB locomotor scale compared to the autologous control group.

Moreover, the parameters of the products according to the present invention, especially the depth of disintegration (which is then re-stabilised), can easily and reproducibly be controlled (FIG. 11A-I).

CONCLUSION

The incidence of peripheral nerve injury in open traumatic wounds of the extremities is approximately 5%. Moreover, tumor resection or congenital malformation might also lead to nerve damage. Consequently, these incidences cause enormous health care expenses, extensive absence from work and chronic disabling. This demonstrates the importance of accurate clinical care of these injuries, because of their considerable high epidemiological impact. Direct repair of nerves is one clinical option in the treatment of traumatic wounds. However, this direct coaptation with end-to-end suturing is limited to short-distance gaps. The current clinical gold standard for the repair of longer gaps is autologous nerve grafting. The main advantage of autografts is their morphologically native structure, which serves as a physical guide for axon-regeneration from the proximal to the distal nerve stump. But autografting impairs several disadvantages such as the limitation in donor sites for graft harvesting or the associated morbidity at the donor site including loss of nerve function, painful neuroma formation and hyperesthesia.

These aspects show that the current gold standard is not an optimal method for nerve repair and therefore alternative approaches to autografts are being extensively researched. Besides nervous tissue to bridge defect gaps, other autologous materials, such as vein grafts or muscles have been tested. However, pre-clinical and clinical outcomes within the past years remain unsatisfactory.

Approaches in tissue engineering (TE) have opened new opportunities in peripheral nerve repair. As a result, artificial nerve guidance conduits (NGCs) composed of synthetic or natural polymers are under investigation for bridging nerve defects. The rationale of an NGC is to entubulate the nerve stumps and the intervening gap to guarantee a protected environment for the new forming nerve tissue.

Despite various synthetic and natural biomaterials being pre-clinically and clinically evaluated for the bridging of nerve defects, their therapeutic benefits are still unsatisfactory.

In the last years, silk fibroin has attracted interest as a suitable biomaterial for peripheral nerve regeneration. In various studies, SF has been shown to compromise numerous potent characteristics that favor its use as an NGC, such as mechanical stability, slow degradation rate, neuro-biocompatibility and its support of nerve regeneration. Besides maintaining biocompatibility, an NGC should fulfill a series of other tasks including its function as a barrier for infiltrating fibroblasts or its mechanical resistance against compression from surrounding tissue. Various methods of producing conduits made from SF have already been described. The objective to generate an SF-based tube in TE is not restricted to the field of nerve regeneration but is also addressed by groups focused on vascular TE. A majority of these approaches in vascular as well as nerve TE use electrospinning to generate tubular structures due to its high controllability. Other techniques include dipping, gel spinning or molding. All the previously mentioned preparation processes are based on SF either processed from aqueous solutions or organic solvents. With the present invention, textile-engineered raw silk constructs are used as raw material for bridging a nerve defect.

In the present examples it was shown that the method according to the present invention is suitable to generate an NGC of SF with distinct mechanical and anisotropic topographical properties and demonstrates its biocompatibility and functionality in vitro and in vivo in a rat sciatic nerve injury model. In the present examples, a nerve guidance conduit (NGC) was produced using a raw silk textile-engineered SF tubular structure as raw material and subsequently treated it with $CaCl_2/H_2O$/Ethanol, FA and methanol. These treatments lead to morphological changes at the surface of the tubular wall, forming a layer of fused silk fibers. As a result of this anisotropy, the elasticity of the SF-NGC drastically improved and cell infiltration into the lumen of the SF-NGC was prevented. In vitro cell culture experiments as well as preliminary in vivo evaluation in a rat sciatic nerve injury model showed promising results, showing that the SF-NGC prepared according to the present invention supports nerve regeneration in a fashion that is almost comparable to autologous grafting—the current "gold standard" for bridging nerve defects in clinics. Further, the use of collagen as a luminal filler in the SF-NGC did not lead to superior results when compared to empty tubes. The present SF-NGC, especially with the addition of a luminal filler containing neurotrophic growth factors and accessory cells, such as SLCs, represent alternative therapeutic methods in the treatment of large neuronal defects, independent of autologous nerve grafts.

The invention claimed is:

1. Method for the production of three-dimensional silk, wherein a three-dimensional silk product is treated with a silk solvent for a limited period of time so that a partial disintegration of the three-dimensional silk product is obtained whereafter the partially disintegrated silk product is re-stabilised with physical β-sheet induction, by treatment with a re-stabilising solution, wherein the re-stabilising solution is formic acid and wherein the silk solvent comprises LiBr, LiSCN, 1-ethyl-3-methylimidazoliumacetate hexafluoro-2-propanol (HFIP), a mixture comprising ethanol and $CaCl_2$, or a mixture comprising methanol and calcium nitrate; or mixtures thereof.

2. Method according to claim 1, wherein ethanol is used in an aqueous solution containing 1 to 50% (v/v) ethanol to partially disintegrate the three-dimensional silk product.

3. Method according to claim 1, wherein the three-dimensional silk product is a woven fabric, a non-woven fabric, a tube, a knitted product or a pressed product.

4. Method according to claim 1, wherein the three-dimensional silk product is a silk fibroin product or a woven product of natural silk fibres.

5. Method according to claim 1, wherein the three-dimensional silk product is made of fibres from silkworm (*Bombyx mori*) cocoon.

6. Method according to claim 1, wherein the three-dimensional silk product is made of reconstituted fibres made of fibroin solutions or recombinant fibroin solutions.

7. Method according to claim 1, wherein the three-dimensional silk product is a medical implant.

8. Method according to claim 1, wherein the partial disintegration is used to provide an anisotropic silk product.

9. Method according to claim 1, wherein the treatment with the silk solvent is carried out at a temperature of 20 to 100° C.

10. Method according to claim 1, wherein the re-stabilising solution is formic acid and wherein the re-stabilised product is further treated with methanol.

11. Method according to claim 1, wherein the silk solvent comprises a mixture comprising ethanol and $CaCl_2$.

12. Three-dimensional silk product, obtainable by a method according to claim 1 comprising at least a stack of two layers of fibroin filaments, a homogeneous fibroin layer and a fibrous fibroin layer.

13. Three-dimensional silk product according to claim 11, wherein the product is a stent, a vascular graft, a nerve conduit, a tissue scaffold or a hernia meshwork.

14. Three-dimensional silk product according to claim 12, wherein the homogeneous fibroin layer has a diameter of at least 20 μm.

15. Method according to claim 1, wherein the formic acid is 90 to 100%.

16. Method according to claim 1, wherein the formic acid is 97 to 99%.

17. Method according to claim 1, wherein the treatment with a silk solvent is carried out at a temperature of 50 to 78° C.

18. Method according to claim 1, wherein the treatment with a silk solvent is carried out at a temperature of 70 to 77° C.

19. Method according to claim 1, wherein ethanol is used in an aqueous solution containing 5 to 40% (v/v) ethanol to dissolve the three-dimensional silk product.

20. Method according to claim 1, wherein ethanol is used in an aqueous solution containing 10 to 30% (v/v) ethanol to dissolve the three-dimensional silk product.

21. Three-dimensional silk product according to claim 12, wherein the homogeneous fibroin layer has a diameter of at least 50 um.

22. Three-dimensional silk product according to claim 12, wherein the homogeneous fibroin layer has a diameter of at least 100 μm.

23. Method according to claim 7, wherein the medical implant is a stent, a vascular graft, a nerve conduit, a tissue scaffold, or a hernia meshwork.

24. Method according to claim 23, wherein the tissue scaffold is a tendon, a bronchi, or a trachea.

* * * * *